United States Patent
Bate et al.

(10) Patent No.: US 12,300,392 B2
(45) Date of Patent: *May 13, 2025

(54) DETERMINING A NEXT-BEST ACTION ACROSS MEDICAL CONDITIONS

(71) Applicant: Evidium, Inc., San Francisco, CA (US)

(72) Inventors: Carl Bate, San Francisco, CA (US); Wian Stipp, Somerleyton (GB); Thomas Unger, Tiburon, CA (US); David A. Epstein, Croton-on-Hudson, NY (US); Matthew McSorley, Pittsburgh, PA (US); Fady Nakhla, San Francisco, CA (US); David Robinson, Santa Cruz, CA (US); Jennifer May Lee, London (GB); Arthur Böök, San Francisco, CA (US)

(73) Assignee: Evidium, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/406,508

(22) Filed: Jan. 8, 2024

(65) Prior Publication Data

US 2024/0153648 A1      May 9, 2024

Related U.S. Application Data

(63) Continuation of application No. 18/135,026, filed on Apr. 14, 2023, now Pat. No. 11,869,674.

(Continued)

(51) Int. Cl.
| | |
|---|---|
| *G06F 40/40* | (2020.01) |
| *G16H 10/60* | (2018.01) |
| *G16H 70/20* | (2018.01) |

(52) U.S. Cl.
CPC ............. *G16H 70/20* (2018.01); *G06F 40/40* (2020.01); *G16H 10/60* (2018.01)

(58) Field of Classification Search
USPC ........................................................ 704/7–10
See application file for complete search history.

(56) References Cited

U.S. PATENT DOCUMENTS

| | | |
|---|---|---|
| 7,379,885 B1 | 5/2008 | Zakim |
| 10,446,273 B1 | 10/2019 | McNair et al. |

(Continued)

FOREIGN PATENT DOCUMENTS

| | | |
|---|---|---|
| WO | 01/069513 | 9/2001 |
| WO | 2012122198 | 9/2012 |
| WO | 2020006495 | 1/2020 |

*Primary Examiner* — Leonard Saint-Cyr
(74) *Attorney, Agent, or Firm* — Beyer Law Group LLP

(57) ABSTRACT

A computational evidence platform extracts clinical concepts from medical evidence sources and creates a database of elemental diagnostic factors and elemental investigations links to medical conditions. Input from a person groups factors and investigations makes corrections and adds a ranking Elemental factors and investigations do not include information specific to their associated conditions but include synonyms and a link to a medical ontology. A patient state is determined by extracting patient known diagnostic factors and investigation results from the patient chart. These known factors and results are matched to the database and a ranking of likely conditions are output. Next-best actions per condition are output by determining factors not yet known and investigations not yet performed. Next-best actions across conditions are determined by performing a recursive tree search of the database and assuming that unknown factors are now known to generate a score for each assumption.

20 Claims, 24 Drawing Sheets

Translation into Computational Evidence

Related U.S. Application Data

(60) Provisional application No. 63/331,526, filed on Apr. 15, 2022.

(56) References Cited

U.S. PATENT DOCUMENTS

| | | | |
|---|---|---|---|
| 10,733,566 B1 | 8/2020 | Chan et al. | |
| 11,437,145 B2 | 9/2022 | Tulley et al. | |
| 11,551,813 B2 | 1/2023 | Tulley et al. | |
| 2002/0002325 A1* | 1/2002 | Iliff | G16H 50/20 600/300 |
| 2005/0010444 A1 | 1/2005 | Iliff | |
| 2009/0192800 A1 | 7/2009 | Brandt | |
| 2010/0145720 A1 | 6/2010 | Reiner | |
| 2011/0119212 A1 | 5/2011 | De Bruin et al. | |
| 2014/0201627 A1 | 7/2014 | Coll | |
| 2019/0198172 A1 | 6/2019 | Nelson, Jr. | |
| 2020/0211692 A1 | 7/2020 | Kalafut et al. | |
| 2021/0004714 A1 | 1/2021 | Neumann | |
| 2021/0142904 A1 | 5/2021 | Michuda et al. | |
| 2021/0321932 A1* | 10/2021 | Borsody | A61B 5/02055 |
| 2022/0344020 A1 | 10/2022 | VanNess et al. | |
| 2023/0335299 A1 | 10/2023 | Tulley et al. | |
| 2023/0386681 A1 | 11/2023 | Tulley et al. | |
| 2023/0410223 A1* | 12/2023 | Dobson | G16H 15/00 |

* cited by examiner

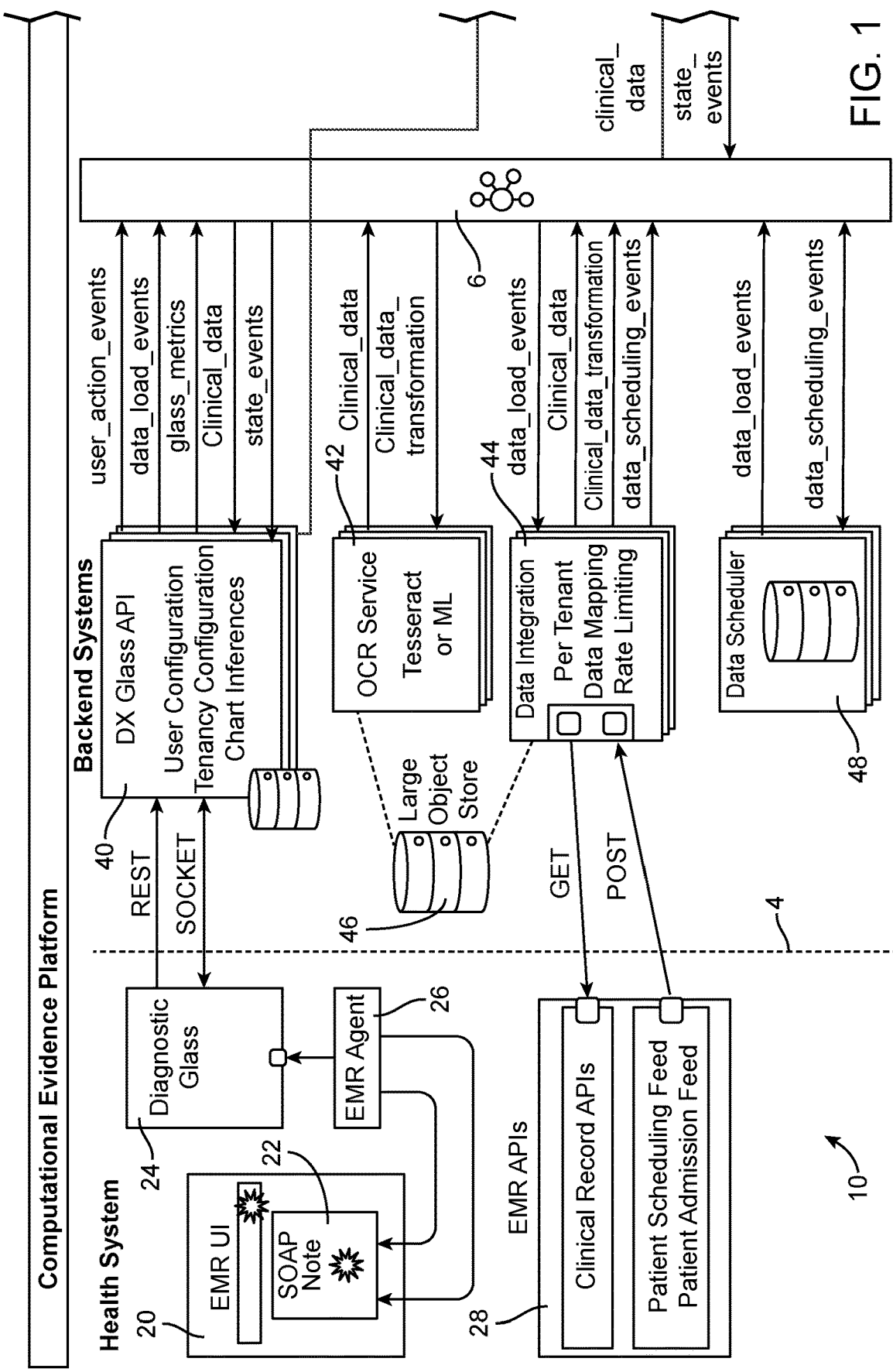

Graph Database Example

FIG. 8A

Data from Record   SORT BY Alphabetical ▾

[Factors] Vital Signs  Lab Results

720 — Pertinent Positives   Add factor ⊕

(abnormal gait⊗) (alcohol use ⊗) (anterior knee tenderness⊗)
(aortic regurgitation⊗)(aortic value disease⊗)(atraumatic fracture⊗)
(back pain⊗)(cardiac disorder⊗)(cardiovascular disease⊗)
(chronic pain⊗)(clicking knee⊗)(congenital anomaly⊗)
(congenital disease⊗)(construction worker⊗)
(decreased capillary refill⊗)(decreased range of knee movement⊗)
(depression⊗)(dermatosis⊗)(dull pain⊗)(emotional state⊗)
(endocrine disorder⊗)(family hx of diabetes mellitus⊗)
(family hx of hypertension⊗)(heart valve disease⊗)
(hx of cardiovascular disease⊗)(hx of dermatosis⊗)
(hx of hypertension⊗)(hx of skin rash⊗)(hypothyroidism⊗)
(intermittent knee pain⊗)(joint effusion⊗)(joint function disorder⊗)

FIG. 8A (Cont.)

☐ <10 Knee bursitis ⌄
☐ <10 Medial collateral ligament injury (Rx) ⌄
☐ <10 Anterior cruciate ligament injury (Rx) ⌄
☐ <10 Septic arthritis (Rx) ⌄

Next best actions
anterior knee pain
[Yes][No]  hx of knee joint effusion
[Yes][No]  BMI 30+
[Yes][No]  Bouchard node
[Yes][No]  high white blood cell count

Data from Record            SORT BY
                                Alphabetical ⌄

[Factors] Vital Signs  Lab Results

Pertinent Positives            Add factor ⊕

(abnormal gait⊗) (alcohol use ⊗) (anterior knee tenderness⊗)
(aortic regurgitation⊗)(aortic value disease⊗)(atraumatic fracture⊗)
(back pain⊗)(cardiac disorder⊗)(cardiovascular disease⊗)
(chronic pain⊗)(clicking knee⊗)(congenital anomaly⊗)
(congenital disease⊗)(construction worker⊗)
(decreased capillary refill ⊗)(decreased range of knee movement⊗)
(depression⊗)(dermatosis⊗)(dull pain⊗)(emotional state⊗)
(endocrine disorder⊗)(family hx of diabetes mellitus⊗)
(family hx of hypertension⊗)(heart valve disease⊗)
(hx of cardiovascular disease⊗)(hx of dermatosis⊗)
(hx of hypertension⊗)(hx of skin rash⊗)(hypothyroidism⊗)
(intermittent knee pain⊗)(joint effusion⊗)(joint function disorder⊗)

Translation Example

Translation Example

[34]

Eyelid and Ocular Surface Disease

Eyelid - Erythematous eyelid swelling is seen in ocular sarcoidosis, which can vary in size from small papules to a large mass.[35] Granulomatous inflammation of eyelids can lead to ptosis, entropion, trichiasis, and madarosis.[36] Selective involvement of Müller's muscle may lead to eyelid retraction.[37]

Conjunctiva - Conjunctival nodules are seen as white discrete conjunctival deposits predominantly affecting bulbar conjunctiva but can also be seen in the perilimbal area and palpebral conjunctiva. [38] In some conditions, the conjunctival nodules mimic acute follicular conjunctivitis.[39] Complications include the development of symblepharon secondary to chronic cicatricial inflammation.[40]

Sclera - Scleritis is a rare manifestation of ocular sarcoidosis and can manifest as diffuse anterior, nodular anterior, or posterior sclerite.[41][42]

Cornea - The most common corneal manifestation of ocular sarcoidosis is superficial punctate keratitis secondary to dry eye (keratoconjunctivitis sicca). Other manifestations include band-shaped keratopathy, peripheral ulcerative keratitis, and interstitial keratitis.[43][44][45]

Uveitis

The mean age of presentation of uveitis is 42 years. Most sarcoid uveitis is bilateral, and approximately 90% are chronic.[46] Uveitis associated with sarcoidosis can be anterior, intermediate, posterior, or panuveitis.

Ocular Sarcoidosis

Extractions
- Corneal manifestations
- band keratopathy
- interstitial keratitis
- keratoconjunctivitis sicca
- peripheral ulcerative keratitis
- superficial punctate keratitis Factors
- ✓ Corneal manifestations
  - interstitial keratitis
  - peripheral ulcerative keratitis
  - band keratopathy
  - keratoconjunctivitis sicca
  - superficial punctate keratitis

SAVE CONDITION

Translation Example

FIG. 9C

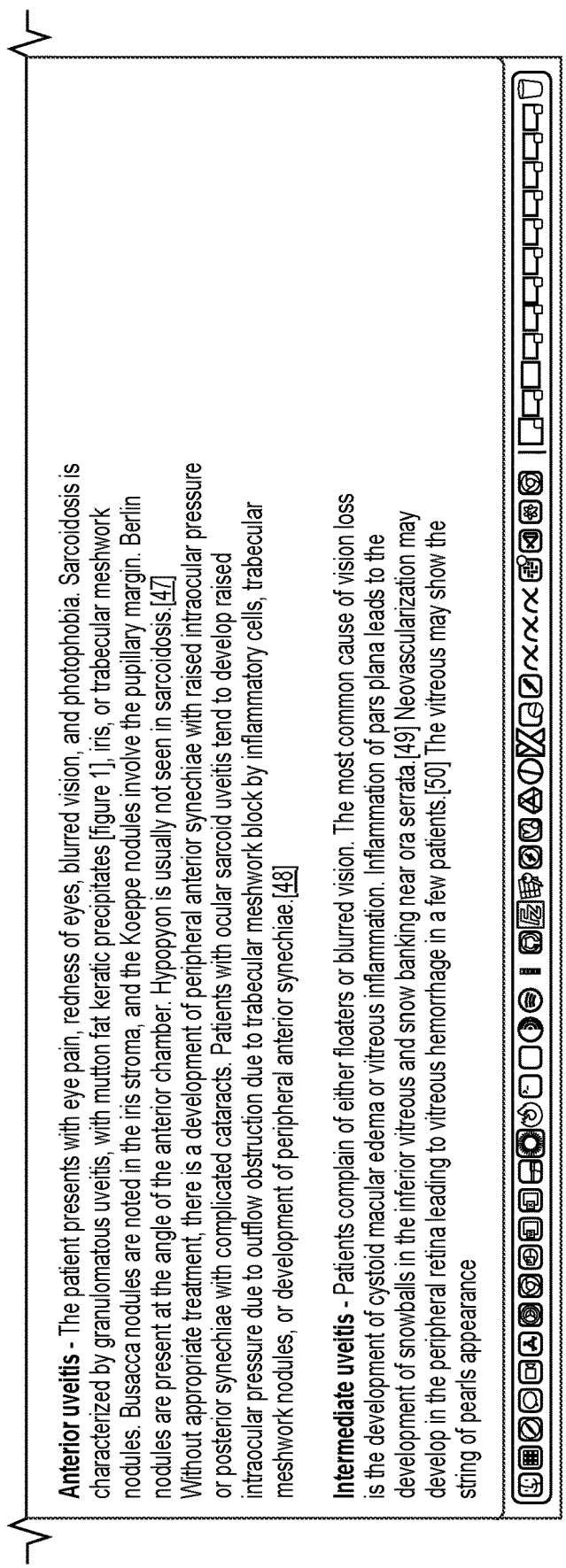

FIG. 9C (Cont.)
Translation Example

Anterior uveitis - The patient presents with eye pain, redness of eyes, blurred vision, and photophobia. Sarcoidosis is characterized by granulomatous uveitis, with mutton fat keratic precipitates [figure 1], iris, or trabecular meshwork nodules. Busacca nodules are noted in the iris stroma, and the Koeppe nodules involve the pupillary margin. Berlin nodules are present at the angle of the anterior chamber. Hypopyon is usually not seen in sarcoidosis.[47] Without appropriate treatment, there is a development of peripheral anterior synechiae with raised intraocular pressure or posterior synechiae with complicated cataracts. Patients with ocular sarcoid uveitis tend to develop raised intraocular pressure due to outflow obstruction due to trabecular meshwork block by inflammatory cells, trabecular meshwork nodules, or development of peripheral anterior synechiae.[48]

Intermediate uveitis - Patients complain of either floaters or blurred vision. The most common cause of vision loss is the development of cystoid macular edema or vitreous inflammation. Inflammation of pars plana leads to the development of snowballs in the inferior vitreous and snow banking near ora serrata.[49] Neovascularization may develop in the peripheral retina leading to vitreous hemorrhage in a few patients.[50] The vitreous may show the string of pearls appearance Translation Example

FIG. 9D

Translation Example

Example Tranformation of Evidence-Based Text to Computational Data

DETERMINING A NEXT-BEST ACTION ACROSS MEDICAL CONDITIONS

CROSS-REFERENCE TO RELATED APPLICATIONS

This application is a continuation of U.S. patent application Ser. No. 18/135,026, filed Apr. 14, 2023, entitled "Translation of Medical Evidence into Computational Evidence and Applications Thereof," which in turn claims priority of U.S. provisional patent application No. 63/331,526, filed Apr. 15, 2022, entitled "System and Method for Computational Evidence," which is hereby incorporated by reference.

This application also incorporates by reference U.S. Pat. No. 11,437,145.

FIELD OF THE INVENTION

The present invention relates generally to automating access to medical evidence. More specifically, the present invention relates to a computational evidence platform allowing any application to query and use the medical evidence.

BACKGROUND OF THE INVENTION

Currently, U.S. healthcare waste is estimated at $1.5 T, and a number of reasons are evident. For one, bias and misdiagnosis are omnipresent, with each of us likely to be misdiagnosed in our lifetime and disproportionately impacted groups due to bias, and the timeframe for new research to be put into practice is 5-17 years. Further, there is already more knowledge than is humanly possible to stay current on and apply, and only 20% of clinical guidelines are backed by high-quality evidence.

Unfortunately, the burden to be more efficient falls on clinicians, who have reached a ~50% burnout rate. Even though evidence is the fundamental unit of diagnosis, treatment, payer economics, research and regulation, current scientific practice and operational medical knowledge is primarily represented as documents in guidelines and computable if-then rules in workflows. This severely limits diffusion, feedback and scalability. And, while powerful, AI architectures based on text alone are not sufficient to represent, process or reason on this knowledge controllably or reliably. And yet further, mapping standard ontologies to documents, for example, as done by existing clinical decision support systems, does not enable controllable use of the information by AI systems. They only provide meta-data to the narrative form.

Physician and healthcare needs for evidence are at an inflection point. Solving this problem is critical to improved (and improving) health outcomes and sustainable healthcare. Current content providers, i.e. publishers, such as DynaMed, BMJ, UpToDate, etc., provide encyclopedia-style medical content look-up for clinicians covering diagnosis, and management of diseases. They assemble the published evidence through expert, human-centric activity—looking at published papers and published society guidelines, sometimes supported by tooling to help human-led assembly activity. These papers are supporting references only. Current best practice takes what are essentially narrative paper documents, even if they are in a digital form, and boils them down to other paper documents, again in narrative form, that require human beings to interpret their contents. This process is slow, inefficient and generalized, although it is the best available, until now.

Another dynamic that puts pressure on traditional referential evidence suppliers is the ability to scale as care evolves to precision medicine. Current referential evidence provides insight at a population level, and will not be able to support individualized assessments and context. Utility of these products to key customers, if remaining unchanged, will decline. For example, future decisions will involve more and more factors: the type of coverage, co-morbidities, individual laboratory values and trends, etc. Current technology is unable to scale within the world of precision medicine. One of the key challenges today is that there is limited post-clinical trial evidence based on the real-world complexity of patient clinical context and response. This in turn perpetuates generalized guidelines, or guidelines that may be harmful.

Medical evidence is the fundamental form of knowledge underpinning the science and practice of medicine. It is used in the understanding, prevention and diagnosis
   of disease. There is no effective way, however, to diffuse, gain feedback or strengthen evidence across the system. Today, evidence is predominantly narrative and document-based for dissemination. This creates significant problems including: delay—there is a 3- to19-year lag from bench to bedside; ineffective at scale—manual search is a time-sink in practice; alert fatigue—documents become hard coded rules out of context; and minimal feedback—there is sparse feedback from practice back to research.

Accordingly, a new platform and techniques are needed to address the above deficiencies.

SUMMARY OF THE INVENTION

To achieve the foregoing, and in accordance with the purpose of the present invention, a platform and associated techniques are disclosed that facilitate the science and practice of medicine, medicine being the understanding, diagnosis and prevention of disease.

The present invention relates generally to making medical evidence computational and usable in a way that can be referenced by any application. In one embodiment, a computational evidence platform allows the extraction of medical evidence or related clinical guidelines from any source and places it into a structured, computational representation system making it useful by any application to query the evidence and to map it to external data inputs such as a patient chart.

In one particular embodiment, a database that includes medical evidence in the form of computational elements may be used by any application useful to the science and practice of medicine, such as clinical decision support, diagnosis, administrative processes (such as prior authorization, scheduling or other), as well as for research purposes. This database may include interlinked computational elements for conditions, diagnostic factors, risk factors and investigations. Prior art techniques place medical evidence into separate silos which cannot be used for reasoning for any medical application.

Embodiments of the invention provide: 1) representing clinical concepts as elemental factors and investigations that are computational useful (i.e., can be shared across conditions) and linking them in a database; 2) determination of the patient's clinical state using these elemental factors and investigations; and 3) determination of the next-best action to recommend for a particular patient based upon his or her state using these elemental factors and investigations. Representing clinical concepts as elemental factors and investigations allows one to compare the electronic health record of the patient to any number of medical evidence sources because the elemental factors and investigations provide a common language for comparison, thus providing an end-to-end link between medical science and the practice of medicine.

BRIEF DESCRIPTION OF THE DRAWINGS

The invention, together with further advantages thereof, may best be understood by reference to the following description taken in conjunction with the accompanying drawings in which:

FIG. 8A illustrates a display of ranked conditions and also next-best actions per condition.

FIGS. 9A-9E are an example illustrating how a portion of an evidence source is translated into computational elements.

DETAILED DESCRIPTION OF THE INVENTION

Figure 1:
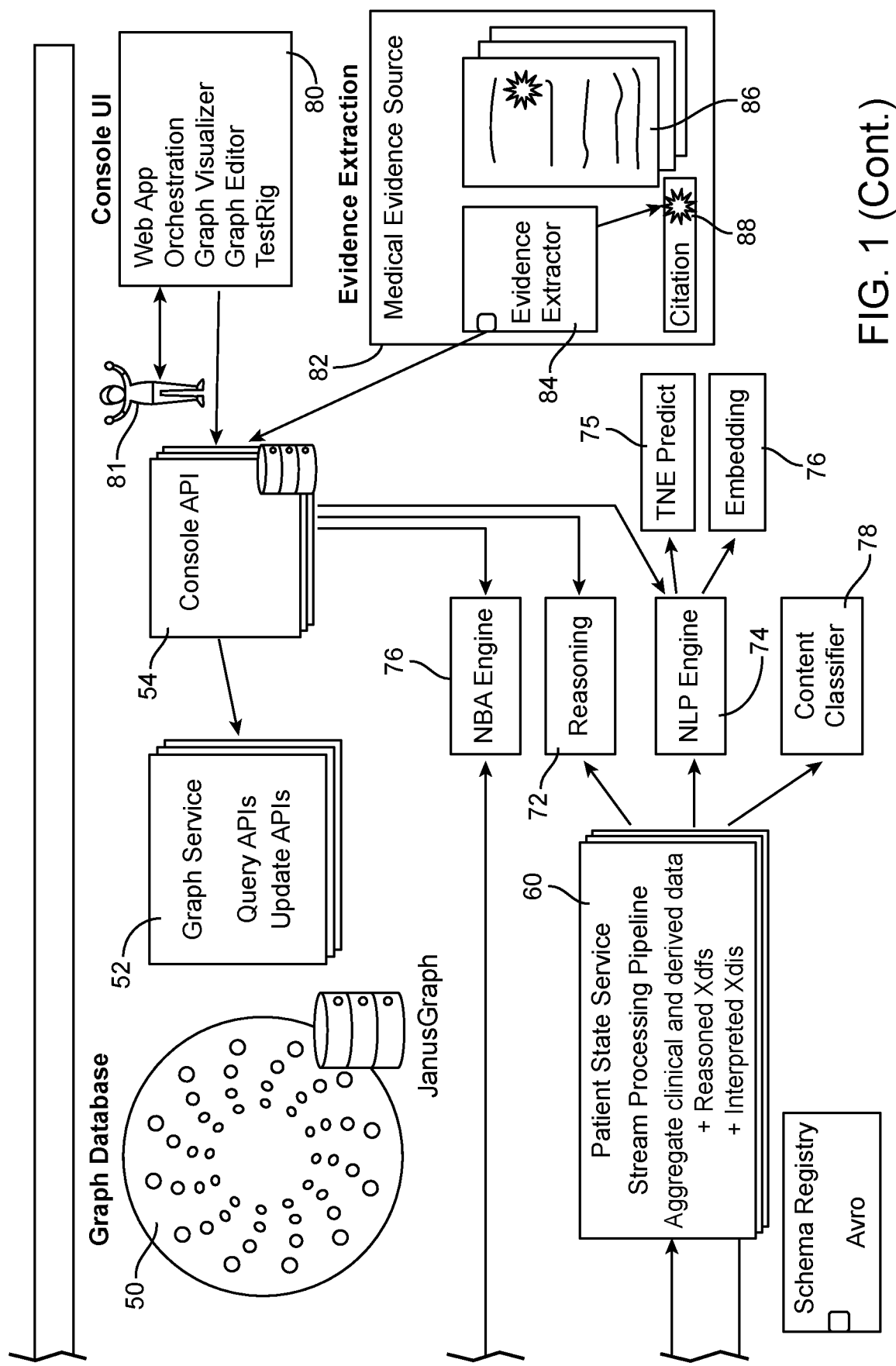
FIG. 1 illustrates a computation evidence platform able to evaluate and diagnose a patient's condition, and recommend a next-best action or actions for that patient, all based upon medical evidence which has been made computational.

While standards exist enabling interoperable exchange of patient data (e.g., FHIR), these standards by themselves do not solve the above problems because they merely abstract sets of queries that can be asked about a patient's state. They do not translate a medical evidence narrative into a structured form of data that is computational.

Some clinical decision support services are available but are less than optimal. By way of example, Stanson Health provides tools, but the difference, and shortcoming, is that at their core they use a rules engine that is limited by the knowledge encoded explicitly in its rules. This is in direct contrast to our approach which is to construct the relationships (via our graph database) between entities which allow for more generalized engines to make broader inferences from the data.

Artificial intelligence (AI) applications are generally separated from the systems in which they are being used in the course of real-time diagnosis by a clinician. This can delay authorizations for testing due to the lack of prerequisite information.

It is realized that multiple clinical ontologies exist, including SNOMED-CT, but that these by themselves do not provide the end-to-end computational representation necessary to make evidence and associated administrative guidelines operational. And although SNOMED-CT provides taxonomies of clinical terms (e.g., fever, heart valve replacements, etc.) it can only perform limited reasoning; while one taxonomy provides a hierarchy of diagnostic factors and another taxonomy provides a hierarchy of conditions, it provides no information as to how particular factors relate to a condition, or how a diagnosis of a patient may be derived using these hierarchies. These are hierarchies of concepts, not relationships, and cannot be used to perform reasoning in order to link a condition to particular diagnostic factors, for example.

By way of example, the condition "ectopic pregnancy" in SNOMED-CT may be described in narrative form as "complications of pregnancy," but it is not connected to a particular factor such as "vaginal bleeding" which would allow inferential reasoning to produce a diagnosis. Further, even if SNOMED-CT could make an inference of presence or absence using certain concepts, a) this only works for defined terms, and b) the coverage in the situation hierarchy is quite sparse in comparison to the concepts covered in the finding/disorder hierarchies.

We disclose converting medical evidence, the "raw material," into computational evidence (or elements) that is application (e.g., artificial intelligence or AI) ready, computational, diffusible and deployable at unprecedented scale and associated functionality utility across healthcare stakeholders. Computational means that elements of medical evidence, relating to the understanding of, and diagnosis of medical conditions, is processable by software applications (including artificial intelligence and other computational models), and combinable with other healthcare data (including patient data and other real-world data), in context and in real time.

Embodiments of the invention are able to combine any number of ontologies and medical evidence sources into one common ground. The underlying database provides computational elements (e.g., factors, investigations) found in medical evidence sources in narrative form (often requiring human interpretation), and the linking of these computational elements with respective conditions (such linking not found in ontologies) allows for computation using the database to provide answers to medical questions.

We believe that the only way to scale the delivery of quality healthcare within the world of precision medicine is to make medical evidence computational by converting it into computational elements. Such computational elements can be used in real time and within the technical and cognitive workflow of the clinician. It will also be able to integrate with, and consider, other sources of information beyond the specialty at hand. Further, feedback loops are able to be much more timely (not simply based upon studies that have been conducted and then published) and can be based on both trials and observational evidence (real-world evidence).

Therefore, we disclose converting medical evidence into computational elements for use in the understanding of, and diagnosis of medical conditions that will have the following advantages. Any medical evidence (such as text or any evidence source) assembled by humans into encyclopedia-style published content may be turned into computational elements, thus effectively turning unstructured content into structured data. This process has limitless extensibility; over time it may scale to include billions of evidence data points and will outpace any referential lookup capability. In particular embodiments the process uses a clinical terminology ontology with pre-coordinated and post-coordinated expressions from SNOMED-CT, uses logical observation identifiers names and codes (LOINC) that gives us reasoning for laboratory tests, and uses RxNORM that gives us reasoning for pharmaceuticals.

Computation Evidence Platform

FIG. 1 illustrates a computation evidence platform 10 able to evaluate and diagnose a patient's condition, and recommend a next-best action or actions for that patient, all based upon medical evidence which has been made computational. Generally, platform 10 may be viewed as having a health system (the user environment) and backend systems, shown separated by vertical dashed line 4. The health system is that hardware and software generally located on customer premises (such as in hospital, clinic, doctor's office, etc.), while the backend systems are generally that hardware and software located at offices and locations owned by or under order control of the provider of platform 10, such as locations controlled by Recovery Exploration Technologies, Inc. or in cloud services such as AWS, Azure, Paperspace, etc. Nevertheless, certain components of the health system (such as the EMR database, not shown) may be located remotely from the clinician (e.g., in the cloud) and in one embodiment the diagnostic glass software application 24 is also cloud based and accessed by a clinician using a Web browser on a computer in his or her office. Other components of the health system may also be cloud based. Note that "clinician" used herein refers to medical doctors, physicians, physician assistants, nurse practitioners and other medical professionals qualified to diagnose, treat and care for patients.

An EMR (electronic medical record) system of record (not shown) is an external database providing the EMR-stored medical data related to the patient and the diagnostic process, including but not limited to patient demographics, symptoms, investigations, examinations, laboratory test results, signs, diagnoses, and history. Data may be accessed in both real time and asynchronously pre-encounter or post-encounter. Data is accessed via various methods including but not limited to FHIR (Fast Healthcare Interoperability Resources) standards.

EMR UI 20 is the user interface of the EMR system; the diagnostic glass application 24 is a stand-alone application that runs on the clinician's computer (e.g., it is a browser application), although it is capable of being launched from that EMR UI 20 environment with a single sign-on authorization including but not limited to SMART on FHIR and other relevant standards. EMR Agent 26 is an event detector that detects user actions on his or her computer. It sends messages via the diagnostic glass 24 to 40 the DX Glass API which in turn is responsible for retrieving the relevant information from the EMR, automatically detects any new relevant data, including but not limited to new data added to the EMR system (for example, a new patient record or state change of patient data such as diagnostic data both in real-time and asynchronous modes of operation), and provides that data to diagnostic glass 24, i.e., data that is typically added by a clinician. EMR APIs 28 is a collection of APIs such as FHIR, USCDI (United States Core Data for Interoperability), CDS Hooks, and vendor-specific APIs which allow EMR agent 26, user interface 20 and other components to communicate with the EMR system. Shown at 22 is a standard SOAP note 22 by which a clinician may enter observations of a patient during an encounter; other data entry techniques may also be used.

Diagnostic glass 24 is a real-time, fully-automated, possibly hands-free software application and user interface, designed specifically to be the system of interaction by which a clinician may enter patient data, and explores diagnoses of a patient either during a patient encounter or when the patient is not present. For example, diagnostic glass 24 is used by a clinician in real time during a patient encounter (live, by telephone, online, chat, video call, etc.) or may be used by a clinician before or after a patient encounter. Diagnostic glass 24 is an interface to the next-best action (NBA) engine 70 which runs in parallel with the clinician's actions and does not require any additional input from the clinician. Diagnostic glass 24 may be used as an overlay or as a window tab.

Diagnostic glass 24 accepts manual clinician entries and selections (e.g., typed input, mouse input, etc.,) and may use speech recognition technology (microphone and speech recognition software not shown) as well as live note capture technology to collect real-time patient encounter information; it also is able to display pertinent positive and negative history from the patient's medical chart in the EMR system that has been extracted by NLP 74 or reasoning service 72. This verbatim text (either from manual data entry, speech recognition, live notes, from the EMR medical chart, etc.) is then converted in real time into diagnostic factors and investigations, and prior conditions all matched to nodes in the graph database 50 by the NLP engine for later use by the NBA engine 70 and classifier 78 to determine potential patient conditions and next-best actions.

In one embodiment, diagnostic glass 24 is an application integrated into the EMR environment via relevant standards such as a SMART (Substitutable Medical Applications, Reusable Technologies) on FHIR application for EHRs (such as Epic and Cerner), and is integrated into the clinical workflow. In another embodiment, diagnostic glass 24 is a standalone system, integrated with relevant external data sources. The suggestions from the diagnostic glass 24 are provided for expert consideration and not as a replacement for the clinician. Thus, the diagnostic glass 24 provides real-time, in-context differential diagnosis and next-best-action suggestions to validate and expand clinical consideration.

Communications channel 6 is a software layer that communicates information between diagnostic glass API 40 (and components 42, 44 and 48) with patient state service 60. Patient State Service 60 is a caching layer that serves to enhance real-time operation for already-analyzed patients and to control access to the various functions provided by the platform. OCR Service 42 provides mechanisms to convert images of text to digital text strings for further analysis. Data Integration Service 44 mediates access to external EHR services including the translation from the abstract data model used by the CEP to the specific data models of the EHRs. Data Scheduler Service 48 provides a mechanism that enables patient charts to be analyzed and cached prior to a patient's visit thus facilitating better real-time performance.

Evidence extraction 82 is performed to extract textual medical evidence from any of a variety of sources for representation within graph database 50. Any of a wide variety of medical evidence sources 86 may be used and include: National Library of Medicine, JAMA Rational Clinical Evidence, BMJ Best Practice (or other British Medical Journal databases), SNOMED-CT (Systemized Nomenclature of Medicine—Clinical Terms), LOINC (Logical Observation Identifiers, Names, and Codes) database, CPT (Current Procedural Terminology) codes, StatPearls content, and laboratory test reference ranges, drug interactions (drug-drug, drug-condition, drug-food), clinical dictionaries, content on rare diseases, and other online sources such as Merck Manuals, WebMD, NORD (raredisease.org), the CDC (for endemic information), the WHO, etc. The evidence extractor can extract clinical items from any textual data source; it maps extracted concepts to these code systems or ontologies.

Typically, the sources used are in electronic form, such as a JSON file, XML file, or other electronic format representing textual information. If they are Web sites then they may be marked up in HTML. The textual information may be free-form text, may be in narrative form, may be semi-structured text (e.g., text within flow diagrams, decision trees, etc.).

In addition, evidence-based medicine sources are used and include a collection of external data, such as datasets of clinical support reference content for healthcare professionals which contain best practices, evidence-based research relevant for clinical decision support including diagnosis and prognosis.

An evidence extractor 84 is a system which extracts relevant text from an evidence source and delivers it to NLP engine 74 for recognition of the clinical concepts within the text. It can be implemented in forms such as a stand-alone application or a Web browser plug-in function. It facilitates the selection, extraction, and delivery of relevant text to the NLP engine 74. The Extractor also facilitates the workflows associated with adding the extracted concepts and relationships into a knowledge management system, in our specific case, the graph database 50. The Extractor itself facilitates the workflow necessary for sending the relevant text, or portion of text, to the NLP for the extraction of domain specific concepts. In the current invention, the NLP is trained in the domain of medical concepts. By way of example, when text related to a particular medical condition is input the extractor extracts the condition, its diagnostic factors, risk factors, investigations, and any differential diagnoses if possible, as well as rankings, etc. The extractor 84 also extracts a citation or citations 88 associated with the extracted text.

NBA engine 70, reasoning engine 72 and content classifier 78 are software modules whose purpose is described below. NLP (natural language processing) engine 74 may include any number of NLP processes (such as an NLP pipeline), each may use a model or not, and each may choose to store information in a wall cache. The NLP processes that may be used include but are not limited to: Word Segmenter, Sentence Segmenter, Negation Cues, Negation Scopes, NER (Named Entity Recognition), Relationship Prediction, NEL (Named Entity Linking), Phrase Extractor, Composite Matcher, Embedding Matcher, Graph Matcher, NLI and Long-to-Long Matcher. The NLP engine may also include models or functions for extracting temporality cues and scopes, experiencer cues and scopes, sex cues and scopes, and age cues and scopes.

NLP engine 74 is used not only for extracting clinical concepts from medical evidence sources, but also for interpreting a patient's chart and outputting factors and results of investigations and in the form of elemental diagnostic factors and elemental diagnostic investigations (EDFs and EDIs).

Graph database 50 is a database that will store the extracted information from the medical evidence sources after that information has been translated into computational elements. Any of a wide variety of other types of databases may be used to store this information such as a relational database or object store or object-oriented database.

In one particular implementation a JanusGraph graph database is used having nodes and arcs, the nodes containing medical evidence of different types (i.e., conditions, differential diagnoses, diagnostic factors, risk factors, investigations,) and the arcs indicating linkages or causality between the nodes. In addition, a citation (or citations) of a scientific publication is extracted per condition and also per factor group, if present. Database 50 may also be referred to as a computational database, a knowledge base, an evidence base, an inferential database, or an inferential database of computational elements.

Console user interface 80 is used by a person 81 and includes a graph editor by which the person views graph database 50 and reviews clinical concepts extracted from the medical evidence, corrects errors (i.e., quality control), adds factors, perform groupings, etc., thus changing and improving the extracted evidence before it is stored into the database 50. It can also be used to update or remove the information once it has been stored in the database. It employs full CRUD capabilities: Create, Replace, Update, Delete.

During determination of the next-best action for a particular patient, patient state service software module 60 keeps track of the patient's state, basically the diagnostic factors and investigations that the patient has presented with (whether from the patient's electronic health record, presented by the patient during the encounter, observed by the clinician, etc.), which may change over time. During determination of the patient state, module 60 will take the factors and investigations extracted from the patient chart and send those to the reasoning service 72 in order to infer other factors and investigations. By way of example, given that the patient has "acute fever" we may also infer that the patient has the factors "fever" and "change in body temperature." For example, it does this using the SNOMED ontology polyhierarchy and walking the relevant ancestor-descendant chains. Note that this can also be done in RxNORM for drugs as well. The reasoning service 72 also contains a component that understands the ancestor-descendant relationships of clinical tests, e.g. CBC with differential is a parent of CBC (complete blood count) is a parent of Hematocrit and White Blood Count.

Not all conditions are described in the literature with the same level of specificity, and similarly, patients may be very specific in their description of symptoms, e.g. a patient suffering from the effects of Botulism might report very specific left upper quadrant abdominal pain, whereas the evidence for Botulism does not localize the abdominal pain to a specific area. Without the inference from LUQ abdominal pain to UQ abdominal pain to abdominal pain a diagnostic factor for Botulism would be missed.

Patient state service 60 may also send the patient state (including any inferred factors from the reasoning service) to the content classifier 78 (or a diagnostic classifier) which performs a straight classification using condition scoring.

Once factors and investigations have been extracted from the patient chart and any inferred factors have been added, the NBA engine 70 executes using as input the patient's current factors and investigations and produces the likely, ranked conditions of the patient, along with for each, unknown factors that should be queried and investigations that should be performed, by referencing conditions, factors and investigations in graph database 50 as will be explained in greater detail below. Thus, the next-best actions for a particular condition may be a question to ask the patient about a specific diagnostic or risk factor, or a specific laboratory test or examination to be performed upon the patient.

Computational Data

In general, the system distinguishes between clinical factors and investigations (including laboratory tests and examinations). A diagnostic factor is a factor that the physician can observe, detect or measure quickly or have the patient describe to him during an office visit (traditional signs and symptoms), while an investigation is a laboratory test or an examination performed by a specialist; both are more sophisticated and take more time. By way of example, diagnostic factors include: "patient has a headache," "patient skin appears yellow," "patient reflexes appear normal," etc. Thus, the value of a particular diagnostic factor may be a simple yes or no, a numerical value, a numerical range, the presence or absence of the diagnostic factor, an observation (e.g., "appears normal"), or other results such as a specific physiological description like "the nasopharynx is symmetric." For purposes of discussion, the system distinguishes between diagnostic factors and risk factors such as gender, age, family history, and medications, e.g., "sex is male" and "family has a history of colon cancer" in order to more accurately output a diagnosis or other goal of the system.

Depending upon the implementation, vital signs, e.g. heart rate, blood pressure, oxygen saturation, etc. may also be considered as investigations. They can be performed quickly, by clinicians with a lower level of education or training, and for little to no cost. Generally, although not always, investigations will be the ones with numbers or numeric ranges whereas diagnostic factors indicate the presence or absence of something.

Typically, investigations require either the collection and processing of some sort of biological sample (a laboratory test) or a physiological analysis using some sort of device (an examination). Laboratory tests may include fluid analysis (e.g., blood panel, urine, semen, and CSF), and examinations may include diagnostic imaging (CT, MRI, X-ray, PET, ultrasound, endoscopy) and pathology analysis among others. By way of example, the result of a laboratory test is "CBC blood test shows reduced hemoglobin level" and the results of an examination is "MRI of the pelvis appears normal." Thus, the result of a particular laboratory test or examination may be a simple yes or no, a numerical value, a numerical range, the presence or absence of a particular item, an observation (e.g., "appears normal"), or other results.

Our design uses EDFs (elemental diagnostic factors) to represent factors, which is a computational element resulting from transforming human-readable evidence into computational elements. Clinical factors described by evidence-based medicine and medical guidelines are translated into EDFs disambiguated across conditions. Specifically, an EDF is a clinical factor that may be evident in a number of conditions, either as caused by a condition (e.g., signs, symptoms, vital signs) or as a risk factor that may contribute to the cause of a condition. Evidence-based medicine typically considers diagnostic factors on a condition-by-condition basis; EDFs enable these factors to be disambiguated across conditions by the system. In cases where the same factor applies to multiple conditions (but may be referred to by different terminology), EDFs enable those like factors to be understood as having the same meaning.

As an example, EDFs may disambiguate clinical factors where one human-readable form relates to "neck stiffness" in one condition and "nuchal rigidity" in another, with the EDF="stiff neck". An example relates to a fever, possibly described in different sources as "being feverish" or "high temperature," but all meaning the same concept. EDFs may also describe higher level factors then the atomic elements, for example "GI symptoms" may be defined as EDFs "nausea", "abdominal pain" and "vomiting". Another example is "constitutional symptoms", with EDFs being "fever", "malaise", and "weakness". Another example is a reference that lists the diagnostic factor "pelvic pain" under the condition "ectopic pregnancy." But, the factor "pelvic pain" is quite broad and we able to extract from the narrative in the reference the very specific EDFs of "acute pelvic pain," "right-lower quadrant pain," "lower abdominal pain," and "pelvic pain." Once "pelvic pain" has been made an EDF, it may be used as a factor for other conditions (e.g., BPH, benign prostatic hyperplasia) which is a male condition).

The graph database, for example, contains the following EDFs that are related to pelvic pain: acute pp, burning pp, chronic female pp, chronic pp without obvious pathology, constant pp, cyclic pp, dull pp, female pp, hx (history) of chronic female pp, hx of cyclic pp, intermittent pp, no female pp, no pp, pp on penetration, sharp pp, throbbing pp, which are all distinct concepts used in various conditions.

These EDFs are part of a computational evidence ontology, which includes other relevant concepts related to conditions and investigations. EDFs are defined in a way that can be applicable across any condition and may be used in any type of consultation such as diagnosis, determination of a next-best action or actions, preauthorization, etc.

The EDFs may also be connected to other ontologies, including but not limited to SNOMED-CT, for example to provide standardized synonyms. A particular EDF may be found in a one-to-one relationship with another clinical concept in a taxonomy such as SNOMED-CT, although many EDFs are created anew and do not exist in other taxonomies.

Each EDF may also have associated a variety of attributes associated with particular conditions such as: age and sex restriction (i.e., if the factor is only applicable to persons of a particular age and only to male or female patients). These condition-specific attributes are held in a demographics node (as shown below) unique to the condition and the EDF, but separate from the EDF. Other conditions having that EDF may have different demographics nodes that are unique to that condition. Thus, EDFs remain elemental, independent, and can be used computationally across conditions.

The EDFs also have attributes defined such as temporality of the factor (historic or present), experiencer of the factor (patient or family member) and negation, whether for a given condition the clinical factor did not occur or is not present. Synonyms defined in an EDF allow the EDF to be recognized across different sources that use different terms. We train the NLP models with the synonyms and they are stored in the database.

Each EDF is also be linked to a taxonomy of clinical concepts (e.g., SNOMED) in order to perform inferential reasoning, such as by reasoning service 72. Inferential reasoning is performed after the initial set of clinical concepts are extracted from any input text or structured data. The NLP process feeds into the inferential reasoning although they may be combined if desired.

Clinical findings in the EHR or other input source are also translated into the relevant EDF. This then enables the clinical state of the patient to be assessed across all conditions in the ontology, and for next-best-actions to be computed, all in the same state-action space.

EDFs are made elemental and independent by placing various attributes that pertain to different conditions into a different data structure linked to both a particular EDF and a particular condition. In this manner, an EDF remains independent and may be used computational across different conditions, yet within the context of a particular condition these attributes are taken into consideration. In one particular embodiment, attributes for a particular EDF relevant for a specific condition are held in a factor group linked to that specific condition and the EDF. By way of example, attributes held in a factor group pertaining to EDFs of a specific condition include: a rank (how likely it is that the condition produces that factor); whether the factor is a risk factor or a diagnostic factor (diagnostic factors are caused by a condition, whereas risk factors tend to cause the condition); and criteria such as whether the condition must exhibit that factor or cannot exhibit that factor. The notion of rank can be further expanded to include sensitivity, specificity, likelihood ratios, incidence, and prevalence among other elements. These all may be combined together to provide an ultimate weight value for the factor group, the weighting being a function calculated outside of a factor group, although the ultimate weight from that function may be stored in the factor group if desired.

One attribute is the ranking of the factor group with respect to its associated condition, i.e., how likely is it that the particular factors of the factor group have been caused by the potential medical condition (in the case of diagnostic factors), or how likely is it that the factor group of risk factors has caused the potential medical condition (in the case of a risk factor). Rank may be expressed in a source using numerical values, or words and phrases to refer to the likelihood that group of factors is caused by particular condition, etc. Other attributes related to rank may include sensitivity, specificity, or a likelihood ratio that may be directly extracted from an evidence source regarding factors of the condition (or that may be added by person 81 reviewing that source). A weight value may be calculated and represented in a wide variety of manners. One technique is to use the ranking only; another technique is to use specificity and sensitivity to calculate the likelihood ratio (the probabilities of people with the factor having or not having the condition). A weighting function calculates the weight value based upon these attributes present within the factor group. Further, demographics that link the factor to a specific condition (e.g., age, sex,) may be held separate from the EDF in a demographics node, thus also ensuring that the EDF remains independent and applicable to any of a number of conditions.

In a similar manner, the design uses elemental diagnostic investigations (EDIs) to represent elemental and independent laboratory tests and examinations which may be used for computation across all conditions. Similar to EDFs, certain attributes of a laboratory test (e.g., a result, units, range, etc.) that are specific to a particular condition are not held within the EDI itself (thus ensuring its independence) but are held separately yet still linked to a specific condition. Further, an investigation group which holds any number of laboratory tests or examinations will have its own attributes defined upon it as well. Further details are below.

Translation of Medical Evidence into Computational Elements

Figure 2:
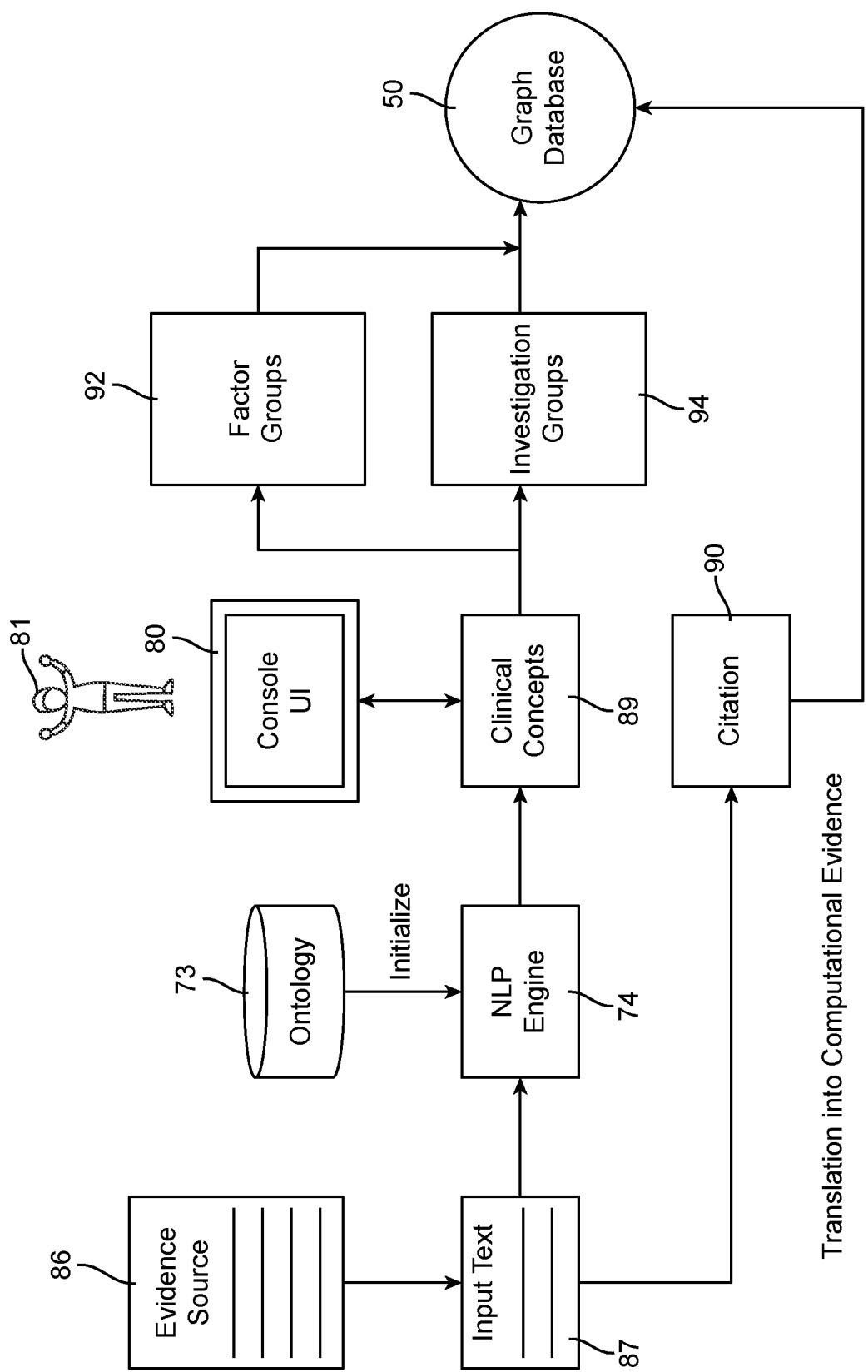
FIG. 2 is a block diagram of further detail of FIG. 1 showing translation of medical evidence into computational elements.

FIG. 2 is a block diagram of further detail of FIG. 1 showing translation of medical evidence into computational elements. Shown is an evidence source 86 from which a portion of input text 87 can be selected and input into NLP engine 74 using evidence extractor 84 as described above. Preferably, NLP engine 74 is initialized using a lexicon such as an ontology (or ontologies) 73 relevant to terms, phrases and concepts in the input text that will be extracted by the NLP engine. By way of example, a lexicon such as SNOMED-CT may be used when the evidence source describes conditions and its factors, an ontology for diseases may be used if the evidence source mainly describes diseases, a specific ontology for a particular disease (e.g., cancer) may be used, or an ontology such as RXNorm may be used if the source describes drugs. Multiple ontologies may also be used. In practice, the NLP engine may make use of nodes in the graph database 50 when recognizing concepts in an evidence source or patient chart.

In one example, the evidence source lists conditions, each with relevant factors and investigations; the clinical concepts 89 extracted are thus the diagnostic and risk factors relevant to a particular condition which are organized into factor groups 92 groups and stored into the graph database 50. To the extent that there are laboratory test results and examinations associate with the condition, these organized into investigation groups 94 and also stored. Using the lexicon or ontology 73 the NLP engine extracts, for example, the most granular descriptions of a particular diagnostic factor that it finds is supported in the input text. By way of example, given a diagnostic factor of "abdominal pain" for a particular condition, in which the narrative describes three specific types of pain such as "lower abdominal pain," "lower right abdominal pain," and "lower left abdominal pain," the NLP engine will extract those three specific types as additional elemental diagnostic factors in addition to the diagnostic factor of "abdominal pain."

Clinical concepts 89, thus, include conditions, factors, investigations, and drugs (trade names and generics). Also extracted from the selected input text is a citation (or citations) 90. We extract also the URL of the source and a hash function which allows us to detect when the contents of the citation have changed in the future. As described above, person 81 uses console 80 in order to review and edit clinical concepts 89 which will be grouped by type and then input into graph database 50. Having person 81 reviewing the clinical concepts output from the NLP engine helps to ensure that the elements of the graph database 50 are sensical and coherent, thus leading to better diagnosis, etc.

Figure 3:
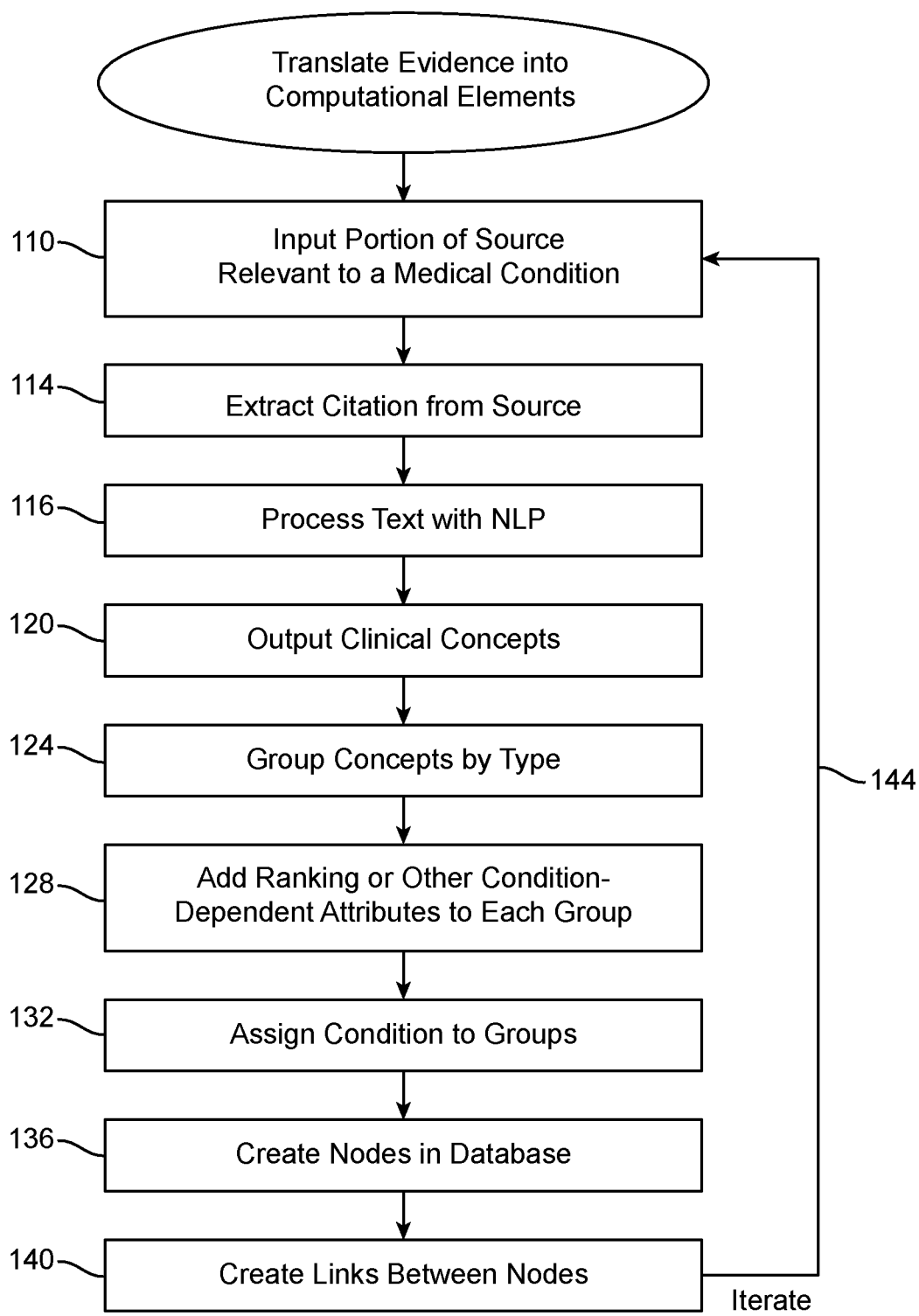
FIG. 3 is a flow diagram describing how medical evidence is translated into computational elements.

FIG. 3 is a flow diagram describing how medical evidence is translated into computational elements.

FIGS. 9A-9E are an example illustrating how a portion of an evidence source is translated into computational elements. These figures will be referred to during the discussion of FIG. 3.

In step 110 a portion of text from medical evidence source is extracted and input into NLP engine 74. In one embodiment, a user may manually choose a portion by highlighting that text, copying the text, or in a similar manner. Or, a portion or portions of text from the source is extracted automatically from the source using evidence extractor 84. Preferably, the source is a respected, clinically-relevant source known to provide accurate medical information. Typically, whether manually or automatically selected, the portion may be a paragraph, section or pages covering a particular condition and its associated diagnostic and risk factors, as well as investigations useful in diagnosing the condition such as laboratory tests and examinations. Or, the portion is a paragraph, section or pages including clinical concepts from any document. Another example is a document including the preauthorization guidelines for an expensive diagnostic test such as an MRI.

Figure 9A:
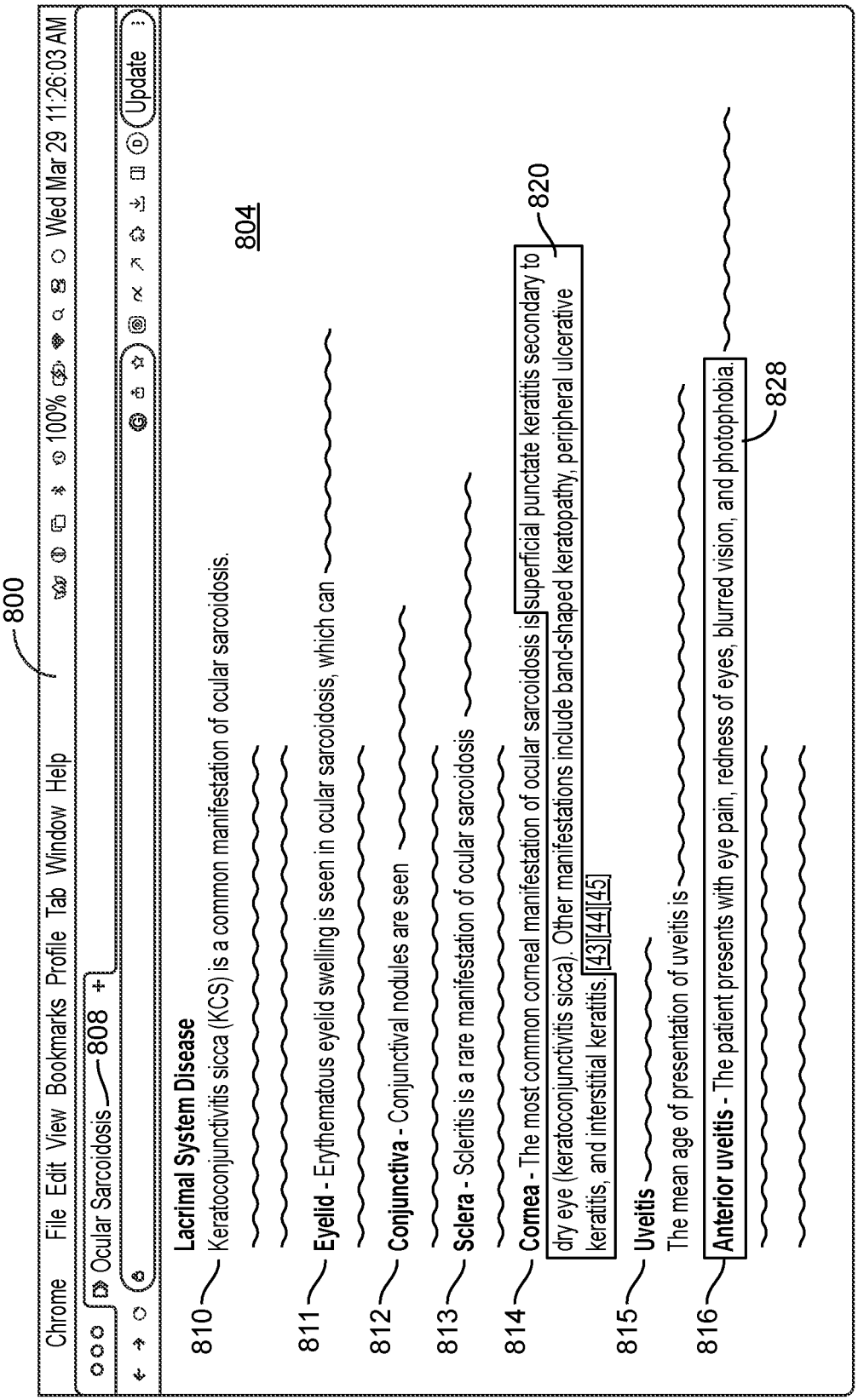

FIG. 9A shows a web browser 800 being used by person 81 who is accessing a particular Web page of a Web site 804 in order to input text for a particular condition 828. The source may be any electronically available Web site, database, archive, file, etc. In this example, the person is reviewing any number of factors 810-816, some listing only a single diagnostic factor, others describing a number of diagnostic factors under each factor. For example, factor 814 lists a number of diagnostic factors which have been selected by the person using box 820. The person may also select the entire narrative for a particular factor, such as by using box 828. The person may also select any number of factors, or investigations, and may also select the entire text pertaining to this condition.

In addition, for each factor a ranking is extracted from the evidence source indicating how likely it is that a factor is indicative of the particular condition, e.g., a positive PCR COVID test is highly indicative that the patient has COVID-19 and such a result will have a high ranking, whereas a patient presenting with a fever is less indicative of COVID-19 and will have a lower ranking Rankings may be later translated into a weight as will be explained in greater detail below. Although a rank is extracted automatically (if available), the rank is reviewed by person 81 who may change it, add a rank to a factor group, re-order ranks of factor groups, etc., thus improving accuracy. Other attributes related to rank that may be extracted for a factor group include sensitivity, specificity, or a likelihood ratio. Again, if these attributes are not extracted automatically the person 81 will review the source text and add these attributes to factor groups, i.e., will order the factor groups by giving them ranks, and may provide sensitivity, specificity or likelihood ratio if that information is present in the source text and has not been extracted automatically.

Rankings are also relevant for investigations as well. Investigations are ordered in how they should be performed, e.g. first line tests—that should be done initially, second line tests that should be done for additional confirmation, and emerging tests that have not yet been fully assessed for broad applicability and/or accuracy. Again, the NLP engine may extract these rankings for investigations but they are also reviewed by person 81 to adjust, change or add a ranking for an investigation group.

Some evidence sources will have explicit rankings, some rankings will be numerical, some will be implicit in the order of factors and investigations for a particular condition, some sources may have no rankings, and some sources may rank differently. Person 81 sets the final ranking of factors and investigations by adjusting rank of a factor group or first line, second line, etc. of an investigation group.

Also extracted for each factor of a condition is a description of the relationship between the factor and its condition (if present in the evidence source). This description does not necessarily define the factor, but rather explains, e.g., how a fever might occur for a specific condition, how common fever is for that condition, or how strong a factor it might be. A condition may be any medical condition, a disease, an orthopedic anomaly, an adverse drug reaction, or a drug-to-drug interaction.

Figure 9B:
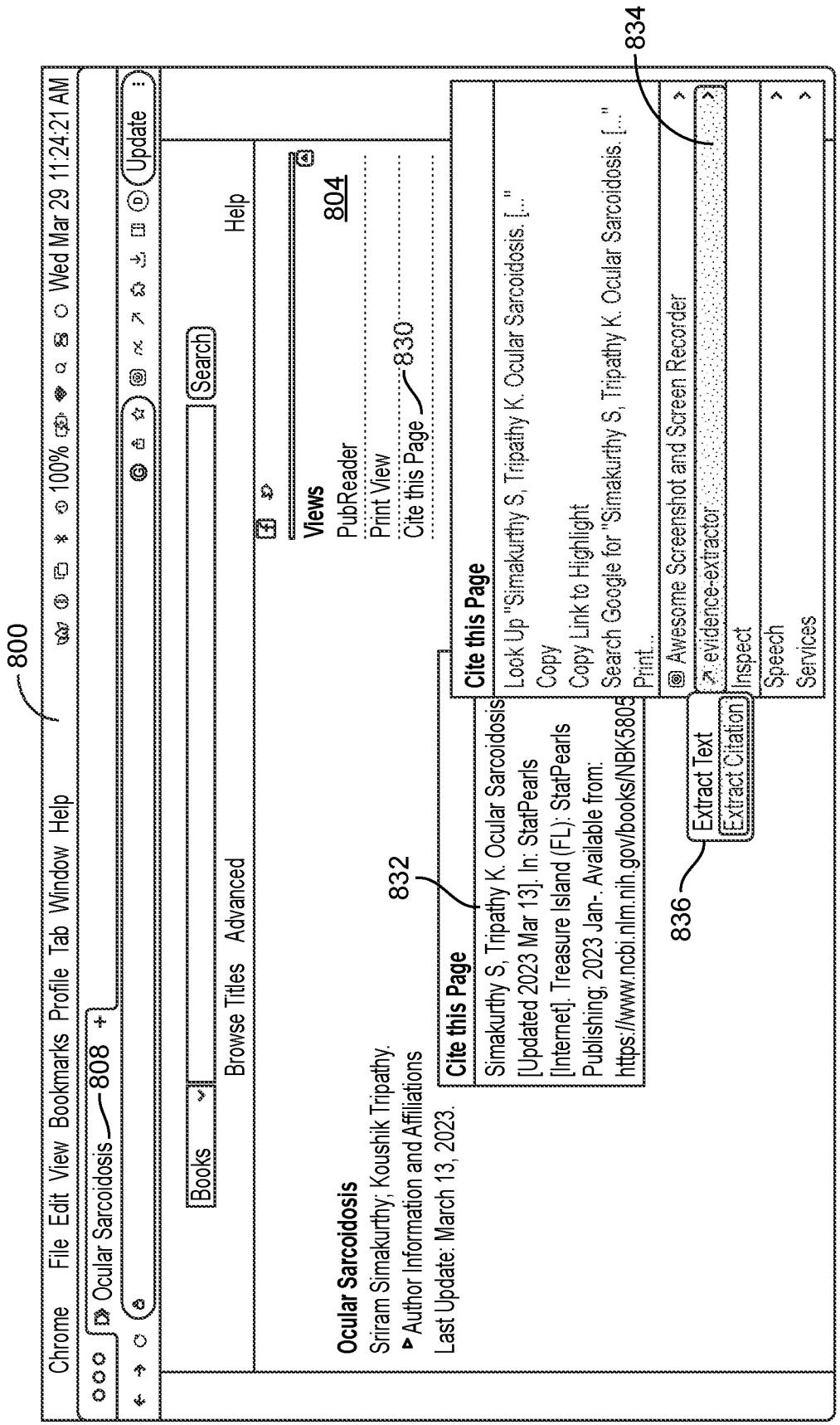

At step 114 the citation (or citations) associated with the input portion is also extracted. FIG. 9B shows that the user has selected option 830, bringing up citation 832, which he or she then extracts using evidence extractor 844 by way of selection 834. Typically, an extracted citation will include: its URL, authors, publisher, title, publication date, any update date, and the full citation.

In step 116 the text input portion is processed using NLP engine 74 initialized with a particular ontology or ontologies tailored for the evidence source as described above. FIG. 9B also shows a selection 836 by which the person may input the selected text into the NLP engine.

In step 120 the NLP engine outputs clinical concepts 89. Depending upon the evidence source used, these clinical concepts may be conditions with their respective diagnostic and risk factors, along with their respective laboratory tests and examinations. FIG. 9C shows that based upon the input text, output are five diagnostic factors 840. Note that these five factors are the finest level of granularity of information that can be extracted from input text, that is, no other factors can be extracted and five is the greatest number of factors that can be extracted based upon this text.

In step 120 NLP engine 74 is also capable of generating elemental diagnostic factors as well. By way of example, if a clinical concept is "abdominal pain" for a particular condition and the text supports sharp pain in the lower left or lower right abdomen, then the NLP engine may generate the EDFs "sharp, lower right abdominal pain" and "sharp lower left abdominal pain." In another example, if a narrative in a source describes "vaginal bleeding" as a sign of an "ectopic pregnancy" and also describes "light bleeding" and "heavy bleeding" as signs, NLP engine 74 is able to produce the new EDFs "vaginal bleeding," "light bleeding" and "heavy bleeding" (along with a ranking for each if available) which will be better able to match a patient's specific signs and symptoms thus leading to a better diagnosis.

Another example is a risk factor for a particular condition that indicates travel to an endemic area along with a description of some of those endemic areas. The general risk factor would be "travel to an endemic area" and the NLP engine would generate a risk factor of "travel to Cuba" assuming that is supported by the text. Another example of extraction is text listing "red eyes and nose" as a diagnostic factor for a particular condition. This text is extracted into "red eyes" and "red nose" in which case red is a part of both factors. Translation of these clinical concepts into EDFs provide highly granular factors and investigations that are truly independent of one another and lead to less confusion and greater accuracy when the graph database 50 is applied to patient information.

Generally, NLP engine 74 is able to extract from the evidence source the most granular factors and investigations supported by the text for a particular condition, e.g., "travel to Cuba" rather than "travel to an endemic area" thus creating computational data. In another example, in a narrative regarding the presence or absence of a fever or history of fever for a particular condition, the NLP engine may extract the clinical concepts "history of fever," "fever," and "no fever," all being separate factors that will be translated into EDFs. The level of detail of the EDF is only limited by the level of detail in the extracted text and what the person 81 may add. In addition to diagnostic and risk factors, clinical concepts 89 produced by NLP engine 74 also include results of investigations such as from laboratory tests or examinations. Clinical concepts may also include drugs, such as the risk factors of "misuse of opioids" or "cocaine addiction."

At step 120 the clinical concepts have been output but are not yet in a computational form, i.e., are not yet all elemental diagnostic factors (EDFs). Typically, the output will be a list of heterogeneous objects, each type of clinical concept having its own data structure, i.e., factors have a different data structure from a condition which is different from the data structure of a laboratory test, drug, etc. These clinical concepts output by NLP engine 74 may also exist within graph database 50, if not, then a new clinical concept may be created to add to the database. Further, a clinical concept need not be a known condition nor a condition already existing within graph database 50; it may be a new condition that will be added as a new node to the database. By way of example, a newly discovered, very rare genetic condition for which some evidence exists may be output as a clinical concept. Typically, the evidence source and input text being processed at a particular time may be limited to particular type of clinical concept (such as factors, laboratory tests, examinations, drugs, etc.) and so the ontology or ontologies used may be specific to the type of clinical concept being processed at that time.

In step 124, the clinical concepts are reviewed by a person 81 using console 80. The person may review the underlying data structures of the clinical concepts or preferably uses a graphical user interface representing the clinical concepts in a more user-friendly form. This person creates groups of factors, groups of investigations, etc., depending upon the clinical concepts extracted from the input text. He or she also decides whether a particular clinical concept remains as a factor group or should become an EDF, or whether a clinical concept remains as an investigation group (e.g., a broad laboratory test or examination group) or should become an EDI.

FIG. 9C also shows that person 81 has created factor group 842 in order to group diagnostic factors 840 together and to indicate to the graph database than a factor group node should be created that will hold five different elemental diagnostic factors. Person 81 also makes corrections, confirms ranks for factors, orders investigations by line, adds new factors or investigations based upon the text, etc. By way of example, if the extraction produces four diagnostic factors from a group of five in the source text, the person 81 upon viewing that text may add the fifth diagnostic factor manually to form a group of five diagnostic factors grouped under one factor group.

Another reason to use a person to review the clinical concepts extracted from an evident source is to correct errors in that source. By way of example, a condition causes a diagnostic factor (e.g., a sign or symptom) but a risk factor contributes to a condition (or even to a symptom); sometimes the two are not classified correctly. The person may change a diagnostic factor to a risk factor or vice versa. The person may also add an EDF for a complex situation, e.g., where the factor is caused by a particular condition which may not already be in a taxonomy such as SNOMED. By way of example, if "pelvic pain" is specifically due to "*Chlamydia*" then the person may create an EDF basically listing the diagnostic factor of "pelvic pain" as being linked to the condition *Chlamydia*.

Person 81 further has ability to add factors for a particular condition based upon different sources. For instance, considering the condition "systemic mastocytosis," one source may list spicy food and acidic foods as being exacerbating factors, while a second source further lists "alcohol" as an exacerbating factor. Person 81 may add "alcohol" as a factor to that condition based upon the second source. Person 81 may also add synonyms for a particular factor or investigation or review and verify synonyms that have automatically been added by the NLP engine. Person 81 corrects errors and classifies the factors correctly so that the causality is clear. Person 81 will also review clinical concepts that include investigations such as laboratory tests or examinations. For example, the person may review ESR or CRP (C-reactive protein) blood tests to make corrections, and information, etc. (e.g., ensure that the test is referring correctly to CRP, plasma CRP or serum CRP). Person 81 may also augment a particular clinical concept in order to add a code or link to a known concept in an established taxonomy of clinical concepts such as SNOMED-CT, thus establishing a cross-link into one or more hierarchies that permit inferential reasoning.

Person 81 also has the ability to rearrange the order of factors and investigations for a particular condition, for example if a particular evidence source is believed to have more or better information. In one example, the input section of text describes the condition "systemic mastocytosis," provides a general diagnostic factor such as "gastrointestinal complaints" and goes on to describe in narrative form some specific factors such as "nausea," "diarrhea" and "abdominal pain." The clinical concepts 89 output then include these three specific factors as factors of that particular condition. Person 81 may then edit any of these factors.

Assuming that the input text was a list of diagnostic and risk factors for a particular condition, the person then selects a group descriptor of "factor groups," decides upon a name for a particular group, and then places those factors that belong to that particular group into that group which may include grouping it some of the factors under one of the factors.

A factor group will be created for each grouping of diagnostic factors. E.g., there will be a factor group for gastrointestinal symptoms, a factor group for headaches, a factor group for fever symptoms, etc. The person will create or confirm these factor groups. He or she may also do the same for investigation groups for laboratory tests and examinations for a particular condition, etc., in the same manner as described above. Thus, factor groups include collections of EDFs, and investigation groups include collections of EDIs. In addition to reviewing or adding the rank for a particular factor group, the person may also review, add to, or change the other condition dependent attributes in a factor groups such as: sensitivity, specificity, likelihood ratio, risk factor or diagnostic factor, must have or cannot have criteria (i.e., for the condition to be present one or more of the subsumed diagnostic factors must be present or cannot be present).

In a preferred embodiment a person does review the clinical concepts, corrects errors, adds factors, perform groupings, etc., thus changing and improving the extracted evidence before it is stored into the database 50. It is important that a person actually reviews and improves some of the clinical concepts. Person 81 will also review any differential diagnoses, make corrections if needed, or add a differential diagnosis from one condition to another if present in the source text, thus resulting in differential link 341, for example.

Further, person 81 also has ability to review, change, adjust, add or confirm demographics information associated with a particular diagnostic factor that will be stored in a demographics node (e.g., node 308 or 374) separate from the EDF. Although the NLP may automatically extract demographics information and separate it from the extracted diagnostic factors, it is helpful to have the person review the demographics information before it is stored into a demographics node associated with an EDF. The demographics information is displayed to the person who may correct it, add information, confirm the information, etc., in the context of reviewing the medical source. Once reviewed, the person saves the demographics information in the appropriate demographics node associated with the EDF. Similarly, although EDI results are also extracted from a medical source along with their corresponding laboratory test or examination, the person will also review the EDI results before storing that information into the appropriate EDI Result node associated with the EDI node.

The person 81 uses the Graph Editor in order to view these clinical concepts in the graph database or may use a different visual editor in order to perform correction and grouping before these concepts are placed into the graph database. These elemental components (elemental diagnostic factors, elemental diagnostic investigations) can often be mapped directly to clinical concepts found in the international taxonomy SNOMED-CT.

Next, in step 128 a rank or other condition-dependent attributes may be added to each factor or investigation group, either by person 81, automatically from the text portion, or reviewed, adjusted or confirmed by person 81. As mentioned earlier, the rank indicates the likelihood that the factor (for example) is caused by the particular condition. The rank may be inherent in the text and be added automatically (e.g., a ranking, term, phrase, percentage, etc. or the text may indicate for each factor the likelihood that it was caused by the condition), or may be added by person 81 based upon their expertise, or may be confirmed or adjusted by the person. In addition, other condition-dependent attributes may be added depending upon the type of each group.

Figure 9D:
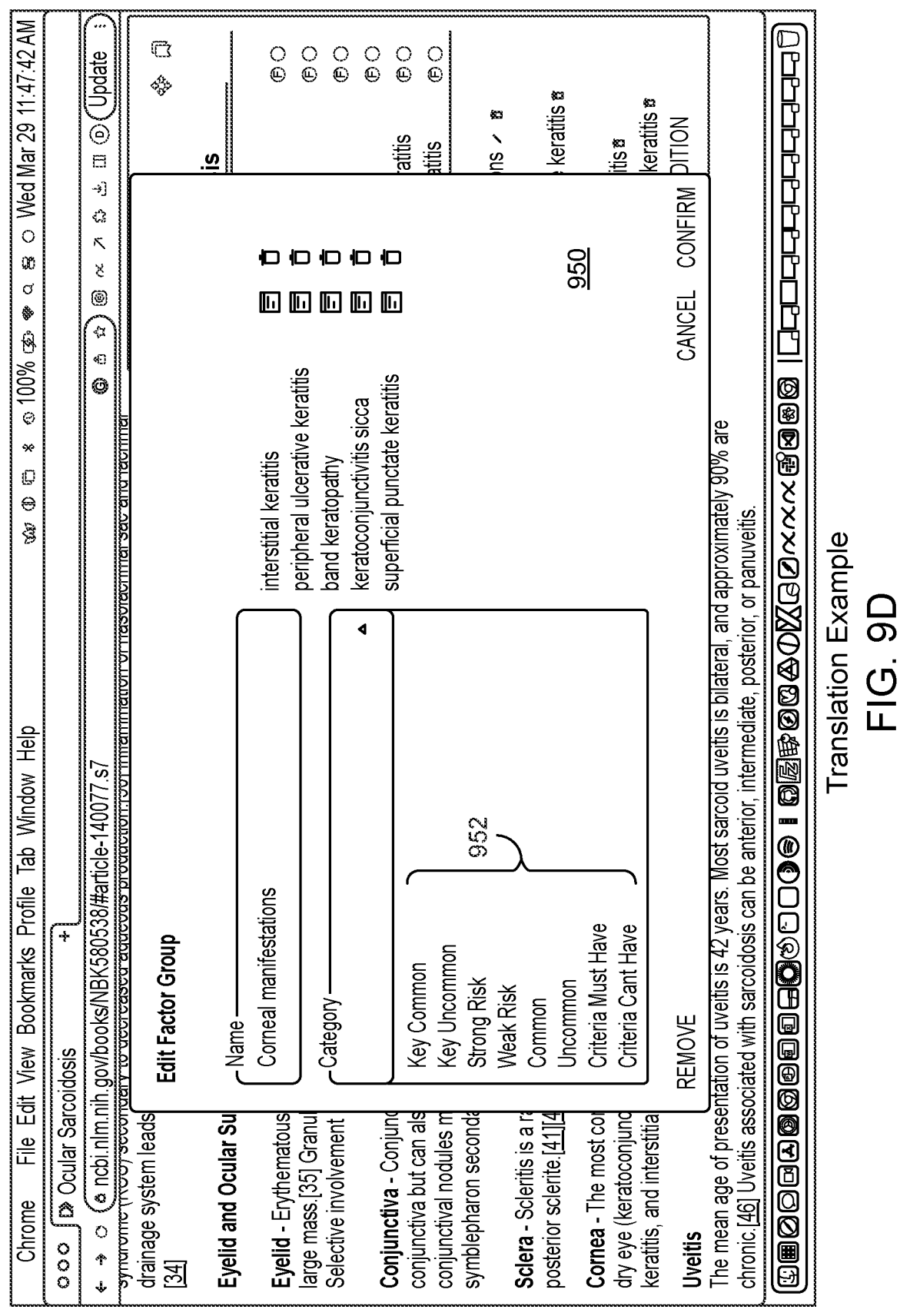

FIG. 9D shows that person 81 is editing the newly-created factor group "corneal manifestations" 950 and may choose to add any of the attributes 952 as shown.

In step 132 the particular condition of the input text is assigned to each of the groups. Each factor group or investigation group will be linked to, or associated with, the condition. Assignment may occur in many different ways, the condition may be part of another data structure which is linked indirectly to each EDF or EDI, or may be performed in other manners. FIG. 9C shows that person 81 has assigned condition 848 to this factor group; this assignment may also occur automatically based upon the context of the input text.

In step 136 the condition, and extracted and possibly modified EDFs and EDIs are stored as nodes in the graph database 50, factors being stored as elemental diagnostic factors in the graph, and investigations being stored as elemental diagnostic investigations in the graph, thus not all the nodes in the graph are EDFs or EDIs. FIG. 9C shows that a new factor group and factors 844 are ready to be stored into the graph database as a factor group and five new elemental diagnostic factors once the person selects 846.

In step 140 links are created between the recently added nodes to the graph database 50. These links (or arcs) show the linkages (or parent-child relationship) between two nodes and may be used to traverse the nodes of the database.

Creation of nodes in the database 50 and creation of links between these nodes may be performed in a wide variety of manners depending upon which graph database is used. Although a visualization of a particular graph database is shown in FIG. 1 (in this example, a property-value graph), other graph databases may be used which are typically implemented using nodes and arcs. Further, a variety of visualizers may be used to view the underlying database and may appear different forms. And, the conditions, factor groups, EDFs, investigation groups, and EDIs, need not necessarily be implemented in a particular data structure shown or as nodes; each may be implemented using the representation of the underlying database. Further, links between nodes need not be implemented using arcs, but may be implemented using any suitable linkage, pointer, reference, etc., according to the underlying database as well.

Figure 9E:
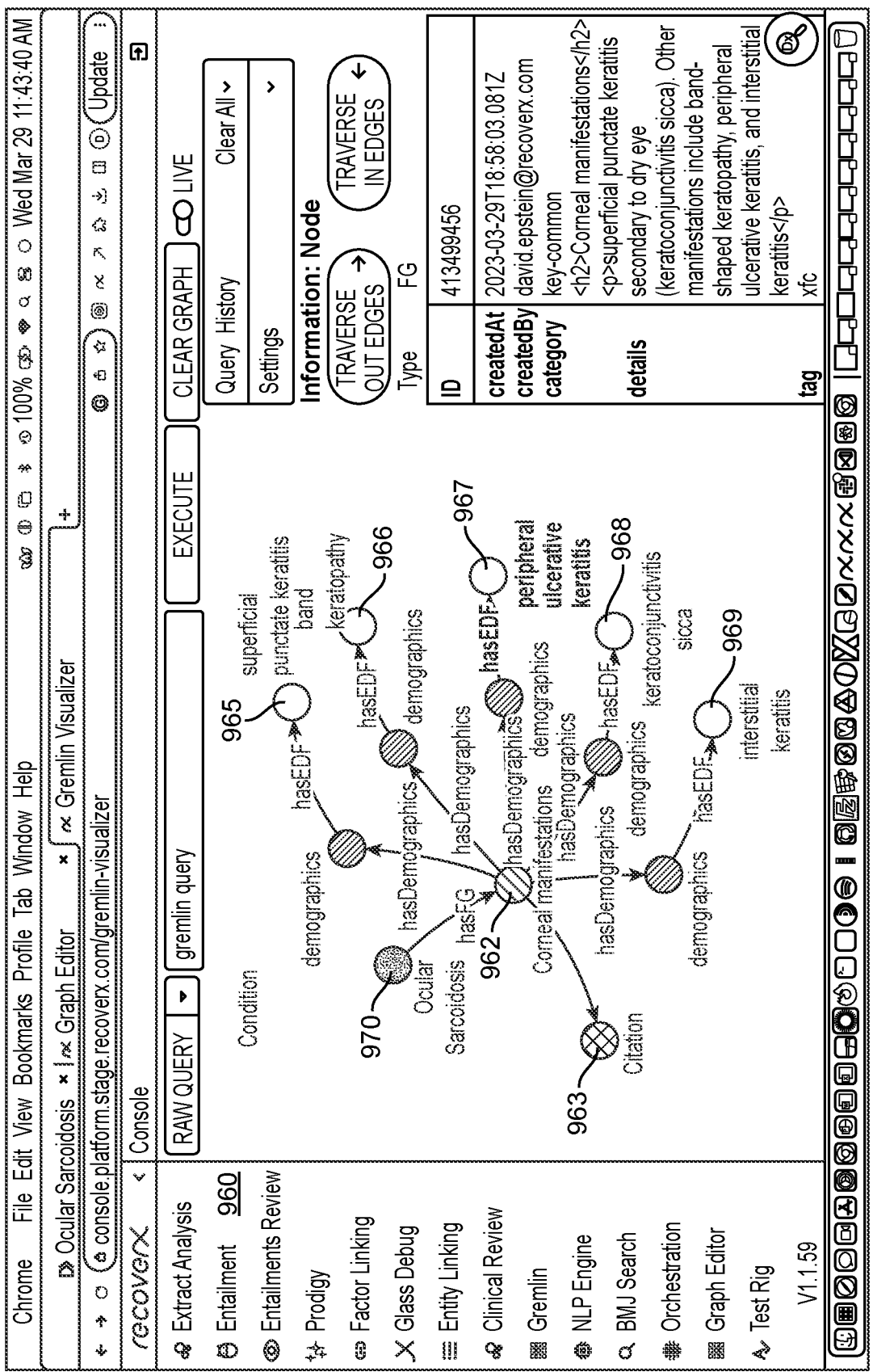

FIG. 9E illustrates how the recently extracted factor group and diagnostic factors are represented 960 in the graph database as nodes. Shown is the factor group corneal manifestations 962 having five EDFs 965-969, each EDF having a unique demographics node. The condition node 970 ocular sarcoidosis is shown having the factor group 962. Factor group 962 also links to a citation node 963 holding a citation with support for the factor group 962 and its factors 965-969 indicating condition 970. As mentioned, each citation may be held in its own node, and other nodes reference that node in order to link back to the citation.

After step 140 the flow may iterate 144 over and over again in order to add other portions of the evidence source, or to add portions from a different evidence source.

Database Example

Figure 4A:
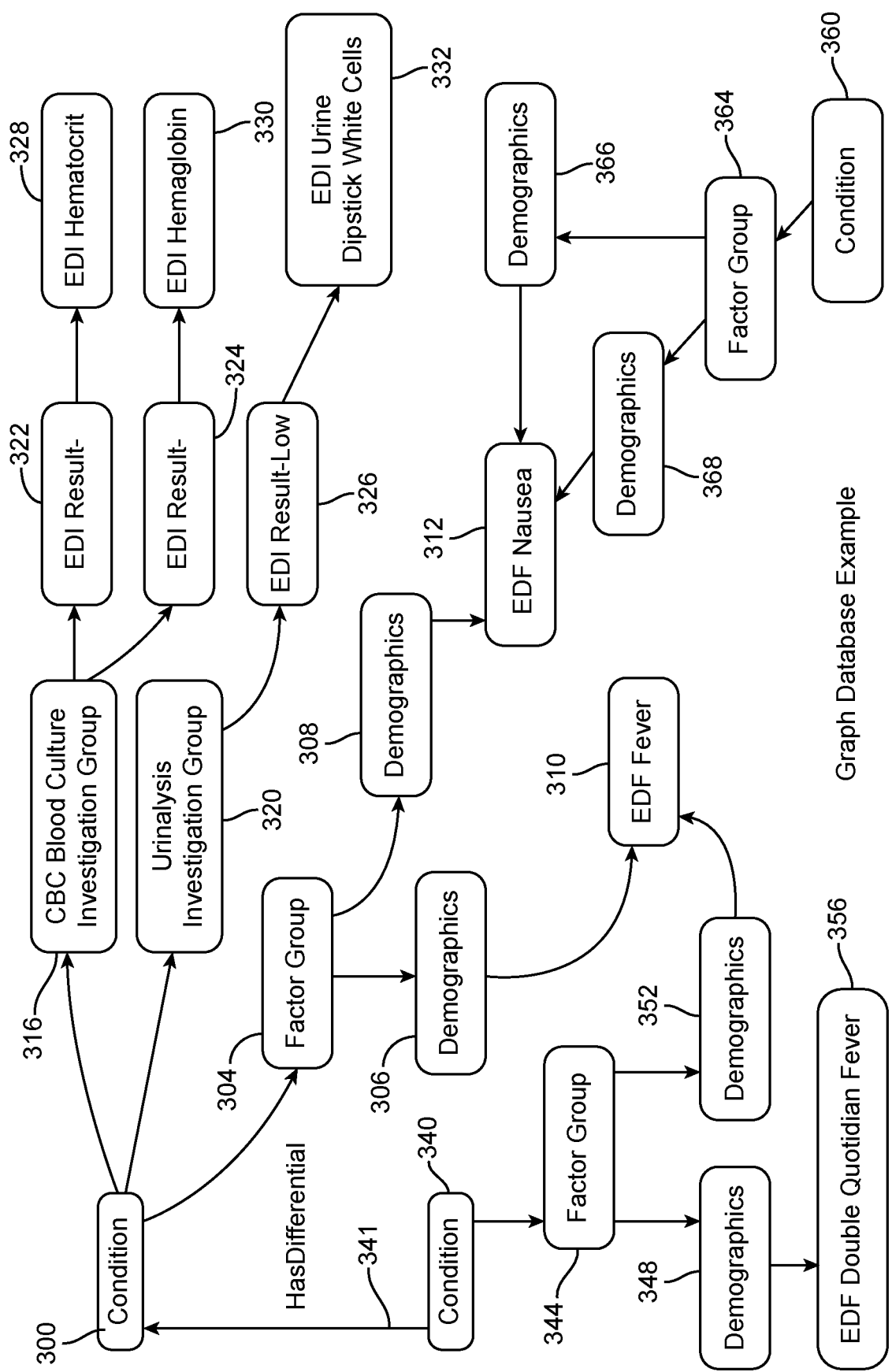
FIG. 4A is an example of a visualization of the graph database after any number of iterations of the flow of FIG. 3.

FIG. 4A is an example of a visualization of the graph database after any number of iterations of the flow of FIG. 3. Shown are specific conditions 300, 340 and 360, each having any number of factor groups or investigation groups. In this example conditions 300, 340 and 360 are specific medical conditions that are not named for purposes of the example. Condition 300 has a factor group 304 including two EDFs, fever 310 and nausea 312, each of those associated with a particular demographics node 306 or 308. The demographics nodes are inserted automatically by the system and there is a single demographics node for each EDF node. Linkages between condition 300, factor group 304, demographics and EDF nodes are provided based upon information gleaned from the steps of FIG. 3. In this simple example, the input text revealed that the factors fever and nausea are diagnostic factors for condition 300.

Condition 340 has a factor group 344 including two EDFs, double quotidian fever 356 and fever 310, each of those associated with a particular demographics node 348 or 352. In this simple example, input text revealed that the factors double quotidian fever and just plain fever are diagnostic factors for condition 340. Note also that the EDF fever 310 is a diagnostic factor for two conditions. Condition 360 has a factor group 264 including one EDF nausea 312 having a demographics node 366 and a demographics node 368; an EDF node may link to multiple demographics nodes. For example, there may be two demographics nodes for nausea node 312 because for this particular condition the factor is only present for the very young (node 368) or the very old (node 366). Other conditions may require two or more demographics nodes for a single EDF or EDI. Note that the EDF nausea 312 is a diagnostic factor for two conditions. In another example, for the condition, abnormal uterine bleeding, there will be two demographics nodes for the factor "women at extremes of reproductive age." One demographic node will have "females 12-19" and the other will have "females 40-60."

Condition 340 also has a related differential diagnosis indicated via link 341 of condition 300. This means that if condition 340 is determined to be present in the patient (as described below) that a differential diagnosis is also condition 300. But, there is no corresponding differential diagnosis link from condition 300 to condition 340, thus indicating that, for this example, condition 340 is not a differential diagnosis of condition 300. Link 341 is added by the person 81 based upon extracting factors and investigations for a particular condition, e.g., the text may say "condition A is often mistaken for condition B." For example, influenza may be confused with RSV because they have the same signs and symptoms. Person 81 using the console will add link 341 if condition 340 might also be condition 300, but will only add a similar link from 300 to 340 if condition 340 might also be mistaken for condition 300.

Condition 300 also has two investigation groups, CBC blood culture 316 and urinalysis 320, both also produced by portions of an evidence source being input into the flow of FIG. 3. Similar to factors, the single laboratory test EDI urine dipstick for white cells 332, is at the end of the linkage, with its possible result, EDI Result low 326, being between nodes 320 and 332. The EDI Result type of node is similar to the demographics nodes in that an EDI Result node provides a result specific to its indicated condition, and is indicative of the condition only when the result has a particular value, such as "low" in node 326.

The other investigation group of condition 300 is CBC blood culture 316 and is an example of an investigation group which may include many specific tests, each having a particular value which is indicative of the condition, if that value is present. Although a CBC blood culture may include many results, only shown are the specific tests EDI hematocrit 328 and EDI hemoglobin 330, each having a particular result 322 and 324. Again, the specific laboratory tests 328 and 330 are only indicative of condition 300 if the results 322 and 324 are as shown.

Advantageously, each EDF has a single (typically) demographics node associated with it that holds condition-dependent attributes that further define how and when a particular factor is present for a specific condition as well as the rank indicating the likelihood that the factor is caused by the specific condition. For instance, if the EDF fever 310 only occurs because of condition 300 in children under 12 years of age, that information is present within demographics 306.

For each EDF the attributes of temporality, negation, and experiencer are also used. Temporality refers to whether or not the patient is experiencing the factor now, negation means the factor is or is not present and experiencer refers to whether the factor is experienced by the patient or there is a family history.

Further, each factor group node holds a ranking as discussed above, e.g., a ranking within factor group node 304 indicates the likelihood that fever 310 is caused by condition 300. Separating out specific demographics and the ranking from an EDF node in this manner allows each EDF node to be truly elemental, independent and atomic in the sense that each EDF node can be referenced and used by any condition; the specifics as to how factor manifests because of a particular condition and its ranking are held in the factor group and demographics nodes, not in EDF node. By way of example, if fever 310 presents itself in a different way for different ages depending upon whether the patient has condition 300 or condition 340, these details are held in demographics nodes 306 and 352 rather than within EDF node 310. And, because fever 310 may be ranked differently for condition 300 and condition 340, these rankings are held in nodes 304 and 344 as well. Thus, a fever 310 in the context of condition 300 is a definition of fever 310 within that node plus its attributes within demographics node 306 and node 304. For certain conditions with bimodal distributions they will be two demographics nodes between fever, for example, and condition 300 (e.g., when the fever only occurs in very young children and in very old people).

The condition-dependent attributes within a factor group node may be added in a variety of manners. Some of the attributes may be automatically added when the factor groups are added to the graph database in step 136 based upon output from the NLP engine when it recognizes the input text. Or, other attributes may be automatically determined by using external taxonomies. Or, person 81 may add attributes to a particular factor when reviewing the clinical concepts in step 124.

In another example, a patient with condition 340 may exhibit double quotidian fever 356 as well as plain fever 310, each being a separate EDF node with its own particular demographics and ranking. This separation of different fevers into different EDF nodes, each having different demographics and ranking allows more accurate diagnosis and reasoning. Because a person with condition 340 may exhibit double quotidian fever and a patient with condition 300 will not, it is important to keep these two elemental factors separate, yet still allow the factor "fever" to be shared by both conditions are shown.

Each EDF node (e.g., such as fever 310) includes a variety of information useful in allowing the node to be elemental and independent as herein described. A node includes its name (e.g., fever), synonyms (e.g., elevated temperature, pyrexia, febrile, feverish, etc.), and a unique identifier that links back to a medical taxonomy (e.g., SNOMED, SNOMED-X, LOINC, RxNorm, ICD, CPT, etc.) and identifies a unique factor within that taxonomy. In the case of SNOMED, the unique identifier may be a SNOMED code or an expression that combines a number of SNOMED codes. The unique identifier to a medical taxonomy allows the system to perform inferential reasoning from the EDF node using the medical taxonomy.

In one example, consider a patient who complains of lower-right abdominal pain but nothing else. If condition X has a diagnostic factor of lower right abdominal pain only and condition Y has a factor of abdominal pain only it will be important to consider both conditions because there may have been miscommunication between the patient and clinician, the evidence source may not be clear, or for some other reason. Accordingly, by using the factor lower-right abdominal pain as an index into the medical taxonomy, one may traverse the hierarchy in order to retrieve abdominal pain as a parent of lower-right abdominal pain and thus assume that the patient also has abdominal pain which may lead to a diagnosis of condition Y. Without that linkage, the clinician or system would only consider condition X.

Figure 4B:
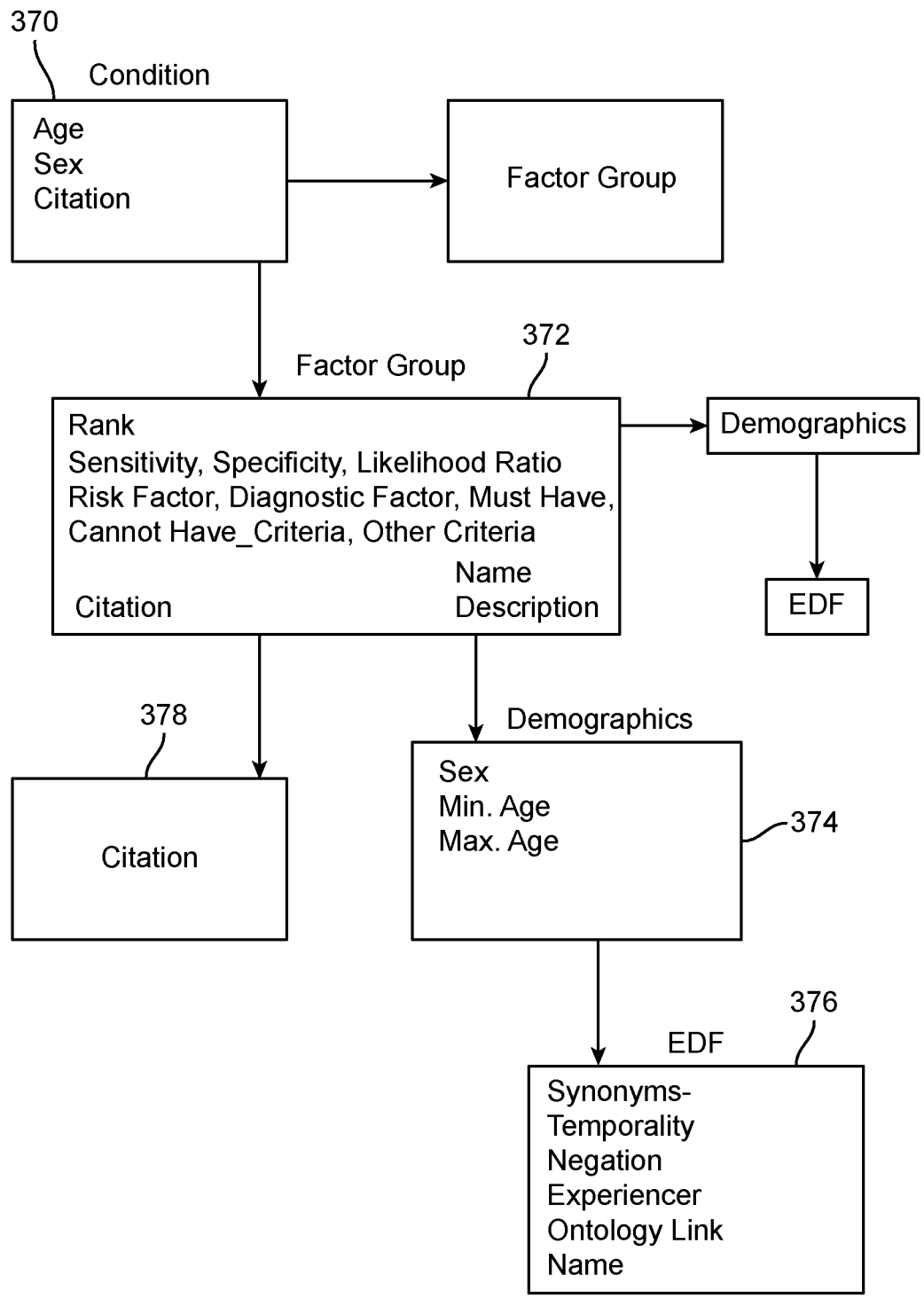
FIG. 4B provides more detail on the content of condition, factor group, demographics and EDF nodes.

FIG. 4B provides more detail on the content of condition, factor group, demographics and EDF nodes. As shown, condition node 370 may include attributes for that particular condition such as age (e.g., the condition can only occur in individuals having an age between 12 and 55), sex (e.g., the condition may only pertain to males or females), etc. Factor group 372 may include a rank (applicable to each of the EDFs to which it is linked), a weight value (which may be used instead of the rank) which may incorporate sensitivity, specificity and the likelihood ratio, a type which indicates whether the EDFs linked below the factor group are diagnostic factors or risk factors, and "must have" and "cannot have" criteria indicating whether or not the EDFs of this factor group must be present for the condition to occur or must not be present. Other criteria may also be present indicating that a certain number of the linked EDFs must be present for the condition to occur (e.g., "at least two of the below diagnostic factors must be present"), or a points system may be used, each of the below factors receiving a number of points and a minimum must be reached before the condition is known to occur. Also included is a link to a citation 378 providing support in a medical evidence source for the use of the factors of the factor group in indicating the condition. Each factor group will also have a name (e.g., gastrointestinal symptoms) and a brief description taken from the evidence source.

Demographics node 374 includes demographics of EDF node 376 which must be true for that factor in the context of condition 370. By way of example, if the factor of EDF node 376 is only present in certain genders, or only below or above certain ages in the context of condition 370 (i.e., the factor can only indicate the condition if the patient meets the demographics) and that information is held in node 374.

EDF node 376 includes only the basic information needed to represent a particular factor (e.g., fever, headache, nausea) such that node 376 is elemental and independent and may be used as a factor in other conditions. By only holding the essential information in node 376, and by holding attributes for that factor that are only relevant to condition 370 in nodes 372 and 374, node 376 can be used as a factor for many conditions. Included are its synonyms (derived from the evidence source or from input by person 81), temporality (T, a binary value indicating whether the factor was experienced in the past or now), negation (N, a binary value indicating whether the factor is present or not present), and experiencer (E, a binary value indicating whether the factor is experienced by the patient or family member). These values for THE may be stored within node 376 or in a separate node linked to node 376. Further, given that there are three binary values, there may be as many as eight EDF nodes 376, each having a different value using the combination of these three values. Each of these eight EDF nodes is also independent and each may be used by many different conditions. By way of example, an EDF node for fever may list temporality is now, fever is present, and experiencer is the patient. A second EDF node fever may list temporality is now, fever is not present, and experiencer is the patient. The other six nodes vary the other two attributes T or E. A link to at least one ontology using a unique code references that same factor within the known ontology providing the ability to traverse the hierarchy of that ontology either up or down.

Figure 4C:
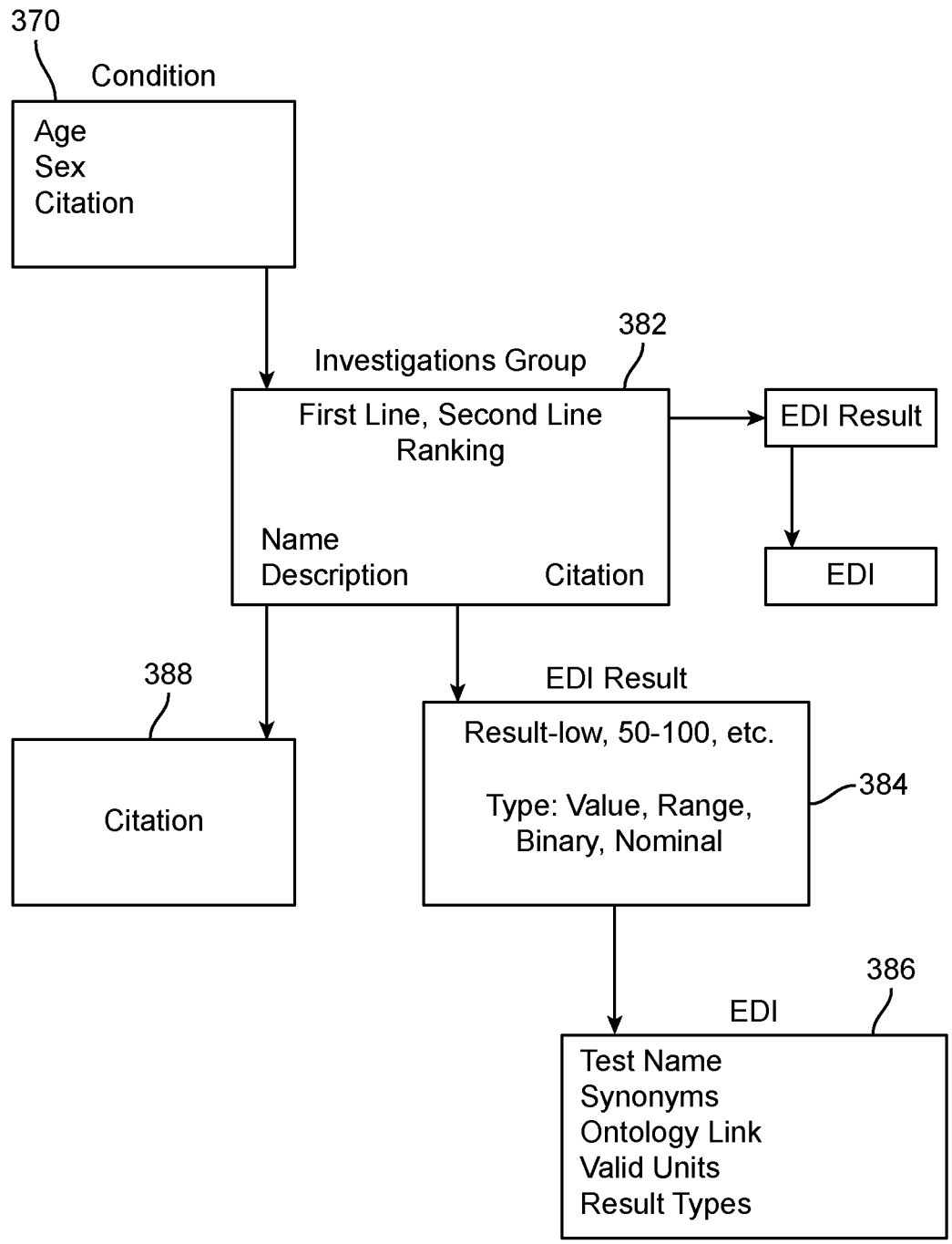
FIG. 4C provides more detail on the content of condition, investigations group, EDI Result and EDI nodes.

FIG. 4C provides more detail on the content of condition 370, investigations group, EDI Result and EDI nodes. As shown, condition node 370 includes the same attributes as above. Investigations group 382 may include a ranking (applicable to each of the EDIs to which it is linked), and also includes a name and description as above. Each investigation group also includes the ranking, i.e., whether the group is first line, second line or emerging, etc., thus ordering the various investigation groups, which ordering may be adjusted by person 81.

Each EDI Result node 384 includes the actual result from the laboratory test or examination (e.g., "low," 32, greater than 100, in-between 50 and 100, yellowish, etc.) to indicate the condition 370, and the type of the result: a value, range, a binary, and ordinal, nominal, etc. Each EDI node 386 includes the test or examination name, its synonyms, a link to one more ontologies using a unique code for that particular test or examination, and all possible result types for that test or examination. Note that the types listed for a particular EDI Result 384 are likely a smaller subset then the result types listed in node 386.

Returning now to a discussion of the investigation groups of condition 300, note that these groups do not have demographics nodes, but each has one or more EDI Result nodes below them which are similar to demographics nodes in that they hold results of tests or examinations that are specific to a particular condition. Nodes 322-326 hold the specific results of a test that indicates when condition 300 is present and EDI nodes 328-332 contain a description of the actual test itself. Similar to EDF nodes, each EDI node include a name of a test (e.g., hemoglobin), synonyms, a link to an ontology.

EDI Result nodes include the result of the test (described using terms such as "high" or "low", using ranges, using binary values, using ordinal types, etc.), units of the result, reference range values, the particular coding, etc., all condition-dependent attributes indicating what is a valid result to indicate the associated condition. Thus, each individual EDI node 328-332 (whether for a laboratory test or examination) remains elemental, independent and may be used computationally across various conditions.

It is realized that because some laboratory tests have different reference range values (and certain machines may have different values), it is advantageous to keep these particular attributes and their values within an EDI Result node rather than within the EDI node itself, thus ensuring that an EDI node (such as EDI hematocrit 328) is truly independent and elemental, and may be used for computation for any condition, not only with condition 300. Other investigations such as examinations are handled in the same manner.

Similar to the relationship between EDFs nodes and demographics nodes, while an EDI nodes such as 328 holds the elemental laboratory test that may be shared between many different conditions, its corresponding EDI Result node such as 328 holds the particular result of that test which indicates that the particular condition 300 is present. EDI node 328 may very well have a different parent EDI Result node having a different result which links to a different condition.

Flow Diagram for Determine Patient State

Figure 5:
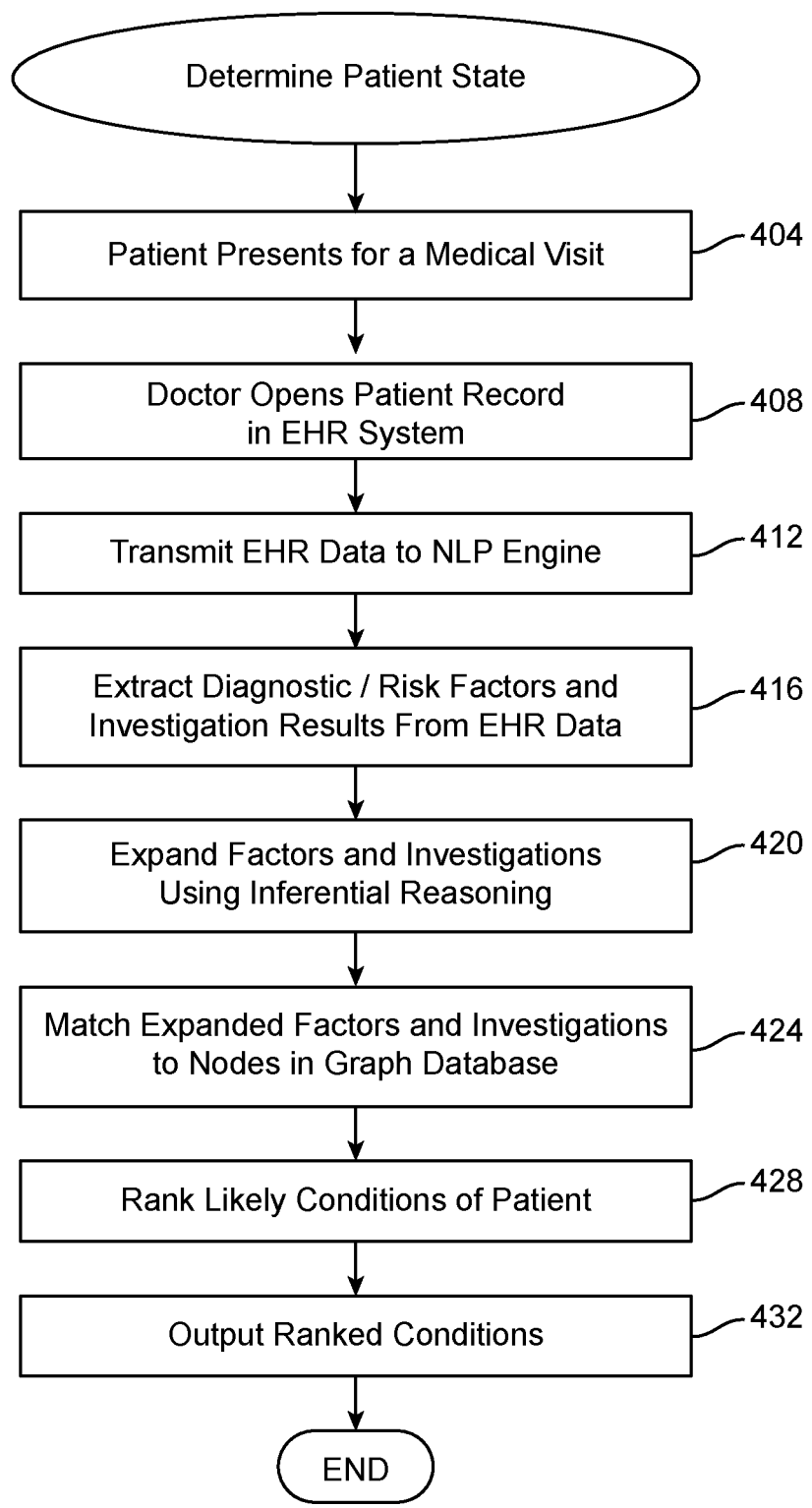
FIG. 5 is a flow diagram describing how the state of a patient may be determined.

FIG. 5 is a flow diagram describing how the state of a patient may be determined. In a first step 404 a patient presents for a medical visit with a clinician, e.g., an in-person visit or the client participates remotely by telephone, computer, or any other suitable telemedicine scenario. Alternatively, the patient has presented in the past and the clinician is reviewing the patient's chart without the patient being present.

In a next step 408 the clinician uses the EHR system user interface 20 (or other suitable user interface such as diagnostic glass 24) to open the patient's electronic chart in the EHR system. The EHR system detects the clinician's context, the patient context (e.g., a medical record number) and sends this information to the backend systems of platform 10.

Next, in step 412 platform 10 via the diagnostic glass 24 (which may be integrated with the EHR system) downloads the patient's medical history from his or her chart and transmits the textual information to the NLP engine 74 via patient state service 60. Included within this medical history are any clinical notes that a clinician had entered previously or has just entered, including simple notes, SOAP notes, structured column notes, consultant notes, etc. Further, any transcriptions may be included as well as transcriptions transcribed from a microphone using speech recognition software.

Next, in step 416 patient state service 60 calls NLP engine 74 in order to extract the diagnostic factors, risk factors and investigation results (including laboratory test results and examination results) from the patient's medical history. Preferably, the NLP engine is initialized with the EDF and EDI nodes from the graph database in order to facilitate finding those same concepts within the patient chart. NLP engine 74 may also use embedding service 76 in order to extract the relevant factors and investigations from the patient's medical history, resulting in factors and investigations that are either known to be present or known to be absent.

Similar to how the NLP engine produced various clinical concepts such as diagnostic factors, risk factors investigations from text from evidence sources, the NLP engine extracts factors and investigations from the patient's medical record and provides them. For instance, if the diagnostic factor "high fever" was extracted from an evidence source as being indicative of a particular condition, and a patient diagnostic factor of "high fever" is extracted from the patient's medical record, both of these factors will be in the same format or data structure thus allowing comparison and a determination that the patient's diagnostic factor matches that same diagnostic factor in the graph database.

The NLP engine produces a patient diagnostic factor (or investigation) that is the same as an EDF (or EDI) in the graph database by matching extracted names with EDF and EDI names and synonyms, and by using the graph database and its links with which it has been initialized. By way of example, the NLP engine may use the ontology link for a particular EDF or EDI in order to explore and match the factors and investigations from the patient's medical record. This is useful when two concepts have the same name but exist in different hierarchies in an ontology (i.e., the same name referring to a condition and the factor). By way of example, given the phrases "cold" or "feeling cold" or "feeling a little cold," these phrases can be ambiguous about whether the patient is describing a condition or a symptom. The engine will use the ontology link in an EDF to understand whether "cold" is a finding (i.e., a factor) or is a condition in the context of the patient's chart. Thus, the engine is able to distinguish between "cold" a condition, and "feeling cold" a patient symptom. During this extraction from the patient chart, the person 81 is not used to extract factors and investigations; it is automatically performed by the platform 10. Basically, the NLP engine is looking for the clinical concepts it extracts from the patient's chart within the graph database that it has built up previously. Further, the NLP engine uses the full context of the patient chart and can distinguish between "patient examination," "pulmonary embolism," and "peripheral edema," all having the acronym PE. Thus, not only is the NLP engine initialized with nodes from the graph database to identify concepts in the patient chart, but also it uses ontology links in particular EDFs in order to disambiguate concepts. Given a concept from a chart, an ontology link from an EDF may also be used by the NLP engine to traverse up a hierarchy of concepts in order to find a concept that it already knows about in the graph in order to match the chart to the graph. All of these techniques provide greater accuracy for the platform.

In step 420 reasoning service 72 uses inferential reasoning in order to expand the diagnostic/risk factors and investigations that were extracted from the EHR data in step 416. The reasoning service 72 may use an internal or external taxonomy or any other suitable medical hierarchy in order to perform this inferential reasoning. By way of example, if one diagnostic factor is "double quotidian fever" the service finds the parent of that which is "fever" and then infers that another diagnostic factor of the patient is "fever." The service will traverse upward in the taxonomy adding all other relevant diagnostic factors that are parents of "fever." In addition, if a negation is present, e.g., a diagnostic factor is "no fever," then the service traverses down the taxonomy to infer that the patient does not have "chronic fever" nor "intermittent fever," and other possible children. In another example of inferential reasoning, if the patient is taking amoxicillin the service also infers that the patient is taking an antifungal medication by traversing up the taxonomy. Investigations may also be expanded. For instance, if the patient did a white blood cell test it may be inferred that this test was part of a CBC blood culture. Preferably, both the EDI node itself and the EDI Result node are expanded.

In step 424 all of the expanded factors and investigations present in the patient are matched to corresponding nodes in the graph database. When we match a patient diagnostic factor of "fever" to the graph database we are matching the patient's factor to the EDF fever node 310 not to its demographics node 306 or 352. The reason being that it is unknown at this time what the patient's condition or conditions might be and by matching only to the EDF fever node it leaves open the option of concluding that any of various conditions linked to fever might be possible. Attempting to match not only to fever node 310 as well as to demographics node 306 might preclude a match if the demographics do not match. By allowing a match irrespective of any of the demographics nodes we can later conclude any potential conditions linked to the fever node, assuming that the demographics match during the analysis. Similar matching occurs with respect to EDI nodes; we match extracted patient laboratory tests and examinations to EDI nodes (e.g. 328-332) irrespective of their EDI Result nodes (e.g., 322-326).

Even though matching only matches EDF nodes, the demographics nodes corresponding to matched EDF nodes are taken into account when reasoning occurs to determine if the patient has the particular condition related to that EDF node. For example, if the patient's factor matches EDF fever node 310, but demographics node 306 indicates that it is only found in women, then a male patient would not be diagnosed with condition 300. Similarly, if demographics node 352 indicates that its associated fever is common in men over 50 years old and the patient is a male over 50, then it is certainly possible that the patient will be diagnosed with condition 340. In a similar manner, EDI Result nodes will be used to determine if matched EDI nodes are relevant for their associated conditions when performing step 424.

In one embodiment, partial matching is performed during step 420. By way of example, as extracted factors and investigation results are each in turn considered for expansion using inferential reasoning, the system will match each to a corresponding node in the graph database in order to find the link to an appropriate taxonomy or hierarchy for expansion. As expansion occurs (either by traversing up or down the hierarchy) the system can match inferred patient diagnostic factors to the corresponding node in the graph database, e.g., inferring that the patient has "fever" from a patient factor of "double quotidian fever" means that the system can also match the "fever" node in the graph database. Matching may occur in other manners, such as by matching all expanded factors and investigations in step 424 rather than during the expansion of step 424.

In step 428 the system computes rankings of the likely conditions of the patient in order to present differential diagnoses. As mentioned above, each factor group or investigation group includes a rank indicating how likely it is that the particular group will manifest given its condition. In addition, each EDF node or EDI node includes a noise value representing how much relevant information content in node has relative to other information. For example, fever node 310 provides a certain amount of information whereas double quotidian fever node 356 is more specific and provides even more information, thus having a greater noise value. Thus, the noise value for fever 310 will be the same for condition 300 as well as condition 340, although the rank of factor groups 304 and 344 will be different.

Step 428 looks at the factor group nodes and investigation group nodes for each matched EDF node and EDI node to determine a ranking of its associated condition. A parameterized weighting function then combines the rank of a group optionally with its noise values (or uses sensitivity, specificity, and a likelihood ratio) in order to compute a weight value for each factor group and investigation group which are then combined to compute a final weight value for a particular condition in order to rank that condition against the other conditions, a higher final value meaning that it is more likely that the patient has that condition.

As mentioned above, even though an EDF node or EDI node is matched, it will carry no weight and the associated condition will not be considered if the patient does not meet the demographics specified in a demographics node in between the EDF node and the condition, or does not meet the specific results in an EDI Result node in between the EDI node and the condition. Further, a matched EDF node will carry no weight and its associated condition will not be considered if the condition-specific criteria in the factor group corresponding to that EDF node are not also satisfied. For instance, if a factor group lists certain "must-have" diagnostic factors then the associated condition will not be considered if those diagnostic factors are not present; similarly, if certain "cannot have" diagnostic factors are listed then the associated condition will not be considered if those diagnostic factors are present in the patient.

Other techniques for assessing the relative importance of EDFs, EDIs, factor groups and investigation groups may also be used. A rank may only reside in the factor group and investigation group nodes, and the sum of all these ranks of all matched nodes is the ranking of the associated condition. Or, we can compute a two- or three-dimensional sensitivity, specificity and likelihood ratio for each group and then compute a total weight for each condition based upon those ratios. In any case, the sum of the likelihoods of matched factors and investigations being present for a given condition informs the final ranking value for a particular condition. The top N conditions may be considered the differential diagnoses for that patient, N being a design choice and being a suitable number for consideration, further calculation or display, such as 3, 5, 10, etc.

In step 432 these top N conditions are output for display upon diagnostic glass 24 for viewing by the clinician, may be output in any suitable data structure for further processing by another software application, may be used as input to determine a next-best action as described immediately below, or may be output for any other purpose. These output conditions may simply be listed in order of their ranking without further information, may each be listed along with a ranking value, may each be listed along with a probability value of being present, etc.

Flow Diagram for Determine Next-Best Actions Per Condition

Figure 6:
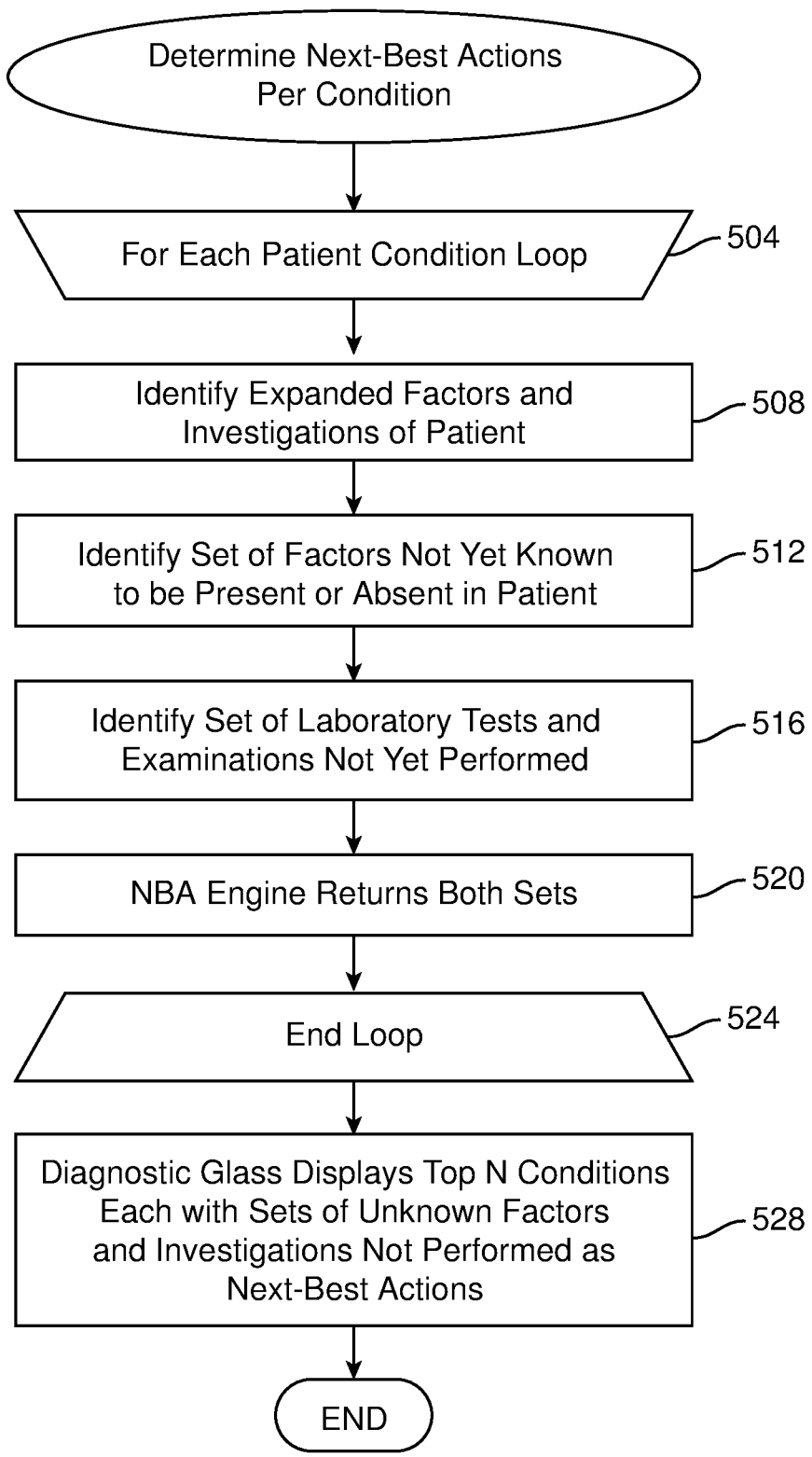
FIG. 6 is a flow diagram describing how the next-best actions per condition are determined based upon the patient's state.

FIG. 6 is a flow diagram describing how the next-best actions per condition are determined based upon the patient's state. Use of the graph database 50 allows the patient's current clinical state to be compared to a body of medical evidence that has been extracted from evidence sources in order to determine next-best actions.

Preferably, the flow diagram of FIG. 5 has been executed and the patient's current clinical state is known, i.e., his or her likely conditions, and the patient's current diagnostic and risk factors as well as results from laboratory tests and examinations that have been performed. These factors and investigations have also been expanded as discussed in step 420 to include other factors and investigations not specifically disclosed by the patient. Alternatively, it is also possible to input a current patient clinical state (i.e., likely conditions, current factors and investigation him results) using other techniques in order to match and identify nodes within the graph database 50.

In step 504 a loop begins for each current condition of the patient with a greater than de minimis probability (identified in step 428 or otherwise), e.g., the top N conditions. Typically, any condition with a probability greater than about 10% will be processed. This minimum is configurable.

In step 508 the NBA engine 70 identifies the set of all of the expanded diagnostic factors known to be present or absent and all expanded investigations known to have been performed, i.e., those identified in step 420—all EDF and EDI nodes in the graph database 50. As mentioned above, these nodes may be identified using an alternative technique and not necessarily from step 420. For example, if the patient presented with a fever and fever node 310 was matched in step 424, then this node is now identified in step 508. Similarly, if the patient had a test performed for hemoglobin, then EDI node 330 is also identified. Step 508 thus produces an identification of all EDF and EDI nodes in the graph database that correspond to the likely current condition.

In step 512 the NBA engine identifies the set of all diagnostic factors and risk factors not yet known to be present or absent in the patient. As step 508 has identified all of the nodes within the graph database that are present within the patient, it is straightforward to identify all of those nodes that are currently unknown. For example, assuming the current condition is condition 300, the engine traverses downward to all factor groups and identifies all of those EDF nodes that have not been matched; if the patient presented with fever but no information is provided regarding nausea, it is unknown whether nausea is present or absent and therefore EDF node 312 will be identified in this step.

Similarly, in step 516 the NBA engine identifies the set of all laboratory tests and examinations that have not yet been performed. Assuming the current condition is condition 300, the engine traverses downward to all investigation groups and identifies all of those EDI nodes that have not been matched; if the patient had performed hematocrit and hemoglobin tests but nothing else, then EDI node 332 will be identified in this step.

Next, in step 520 the NBA engine returns both sets of unknown factors and not-yet-performed investigations for the current condition and holds these results until the loop ends. In step 524 after all patient conditions have been processed the loop ends and the NBA engine may return both sets for all conditions to diagnostic glass 24 for display, may provide both sets to patient state service 60 for storage or later processing by another application, or may retain both sets from all conditions for further processing in FIG. 7 below.

In step 528 the diagnostic glass displays to the clinician these top N conditions each with a set of factors not yet known to be present or absent in the set of investigations not yet performed as the next-best actions. Preferably, the listing of the next-best actions (whether factors or laboratory tests for examinations) are listed in the order of their importance to a particular condition, such as by using their calculated weight or ranking from a factor group or investigation group. This weight or ranking may be listed explicitly alongside each factor group or investigation group when displayed or may be implicit in that factors and investigations are listed from top to bottom in order of decreasing weight or rank. For example, the rank of EDF fever node 310 is found within factor group 304 and the rank of EDI hemoglobin node 330 is found within investigation group 316.

Other techniques for displaying this information may also be used. For example, the number of conditions presented may be configured in a variety of ways including but not limited to a specific number of conditions or by using a specified weight threshold. Or, the conditions may be ordered by their weights as established by NBA engine 70. The information may be displayed within diagnostic glass 24, within a similar standalone product, or integrated with the EHR system. The present, not present and unknown clinical factors associated with a particular condition may be displayed with an indication as to their particular state. The unperformed laboratory tests and examinations may also be listed with their current state (i.e., unperformed). The next-best actions may be presented either per condition or in the aggregate. The presentation of the information by the diagnostic glass user interface may be textual, graphical, audio, video, a combination of the above or in another appropriate format.

Further, while in one embodiment the output next-best-action factors to query are ranked against one another while the output next-best-action investigations are similarly only ranked against themselves, in other embodiment both may be ranked against one another, e.g., the first next-best action may be an unknown factor while the second next-best action may be a recommended test or examination.

Flow Diagram for Determine Next-Best Actions Across Conditions

Above is described a technique for determining the next-best actions per condition, the below flow diagram describes a technique for determining the next-best action across all the conditions that the patient may have, or list of the top N next-best-actions. In other words, these next-best actions are the best action or actions that a clinician can take (e.g., the best diagnostic or risk factor the clinician should ask about, or the best laboratory test or examination to perform) in order to most quickly diagnose the patient's condition. Using the example of FIG. 4, if the patient presents only with a fever this means that the patient has condition 300 or condition 340. The next-best-action will be to ask if the patient has nausea (matching to EDF node 312) and if so, this means that the patient has condition 300, and if not, it is likely the patient has condition 340. Another possibility is to ask the patient to perform a hemoglobin test (assuming EDI node 330 is currently unknown), and if positive, this means that the patient likely has condition 300, while if negative, means the patient likely has condition 340. Of course, an actual graph database will be much more complex and contain many hundreds of thousands of nodes or more, meaning that an automated search algorithm is used.

In a first step 604 the current unknown factors (i.e., not known to be present or absent) and investigations (i.e., those not yet performed), corresponding to the patient's current state are identified. In addition, their corresponding nodes in the graph database are also identified, i.e., the unknown EDF and EDI nodes. Preferably, this step is performed using the results from step 504-520 of FIG. 6, i.e., those sets of unknown factors and investigations.

And, although step 604 appears outside of the search algorithm loop in this flow diagram, it is also possible to identify these unknown nodes during the search algorithm loop while the algorithm is traversing nodes of the graph database. In other words, as the patient's state is known (i.e., the NBA engine knows which factors are known, and which investigations have been performed), it is also known which nodes are unknown and these may be identified as needed in step 612, 616 and 628.

In step 608 the search algorithm is begun using the graph database and knowing the patient state (i.e., which nodes are known and which are unknown). Any of a wide variety of search algorithms may be used, especially tree search algorithms, and one that has been found to work well is the Monte Carlo tree search. Even a brute force search may work but will take more time and resources.

Next in step 612 one of the unknown nodes is chosen to begin, the "next node." For example, if it is unknown whether or not the patient has nausea, then EDF node 312 may be chosen to be the first node with which to begin.

In step 616 given the patient's current state, the search algorithm assumes that this next node is now known (e.g., "patient does have nausea") and new condition rankings are generated based upon this new information. This step may be implemented as in steps 420-432 in which the new, now known factor is expanded, these are matched to nodes in the graph database and new rankings of the likely conditions are generated based upon the original patient state plus this new information. Further, this step is also able to take into account the probability that a patient would respond "yes, I have nausea."

This step also generates a new score, effectively evaluating how beneficial it is in assuming that the next node is now known in terms of determining the patient's condition; the score represents how effective that assumption is in distinguishing the conditions from one another. In one embodiment, the score represents how much the differential diagnoses have changed relative to one another. For instance, if in the patient's original state one diagnosis had a probability of 70% and a second diagnosis had a probability of 75%, but, once the assumption of "patient does have nausea" is made the first diagnosis has a probability of 95% and the second diagnosis now has a probability of 60%, the score for that assumption will be quite high. If both diagnoses are now at 70% then the score will be lower. In addition, the search algorithm will also generate a search branch and a corresponding score where the assumption for that next node is the opposite, i.e., "patient does not have nausea."

The score may also be interpreted as an attempt to maximize the confidence in a potential patient condition using the minimum number of actions (e.g., questions, laboratory tests, etc.). Typically, the score per action is a combination of the dollar cost of performing the action (asking about a diagnostic factor, performing a laboratory test or examination), the time involved in performing the action, and the risk of performing the action. How these are combined to yield a particular score will depend upon the implementation. By way of example, asking about diagnostic or risk factors typically has no cost, little time and no risk, while laboratory tests may have minor costs, sometime involved and low risk. More complex examinations (such as an MRI) may have high cost, significant time involved, and greater risk. These score factors may be held within individual EDFs or EDIs, may be held in association with these via a link, may be held in a separate database cross-referenced to the individual EDFs and EDIs, or in similar manners.

In step 620 this generated new score will be stored with reference to unknown node about which an assumption was made and may be compared to previous scores for previous assumptions made for other unknown nodes. As is known in the art of search algorithms, and especially recursive algorithms such as the Monte Carlo tree search, the search will continue down these two paths, one assuming nausea and one not, generating new condition rankings and new scores as it goes. Further, a search algorithm such as the Monte Carlo tree search will also trim (or prune) nodes for which an assumption would be irrelevant, may discard the current search path, and may eventually return to a state where EDF node 312 is again unknown and will make an assumption for another node.

Accordingly, in step 624 a decision may be made to terminate the algorithm. The algorithm may be terminated based upon user input indicating that only a certain number of seconds or fraction thereof should be used in performing the search, based upon only a certain number of levels of recursion should be used, may be terminated once a particular score threshold has been reached, may be terminated once a particular score is a certain quantity greater than the next largest score, etc. If not terminated, then in step 628 the algorithm chooses a new next node from among the unknown nodes identified in step 604 and recursively continues its search by returning to step 616. As known in the art of search algorithms, this next node may rely upon assumptions made for other unknown nodes, or may revert to the original patient state and choose a different unknown node to make an assumption about it.

If the algorithm does terminate, then in step 632 a list is output of the top N unknown nodes having the highest scores from highest to lowest. The nodes may be listed inherently in order or may have the numerical score associated with each one. In other words, since the NBA engine keeps track of the score generated each time a particular unknown node becomes known in step 616, it is able to output this list which may be a single EDF or EDI node, or multiples of these nodes, thus representing the next-best action or actions across all possible conditions of the patient. Once output, the clinician is thus able to query the patient about an unknown diagnostic or risk factor, or order a particular laboratory test or examination to be performed which will result in the best way to reach a diagnosis at that time.

Figure 7:
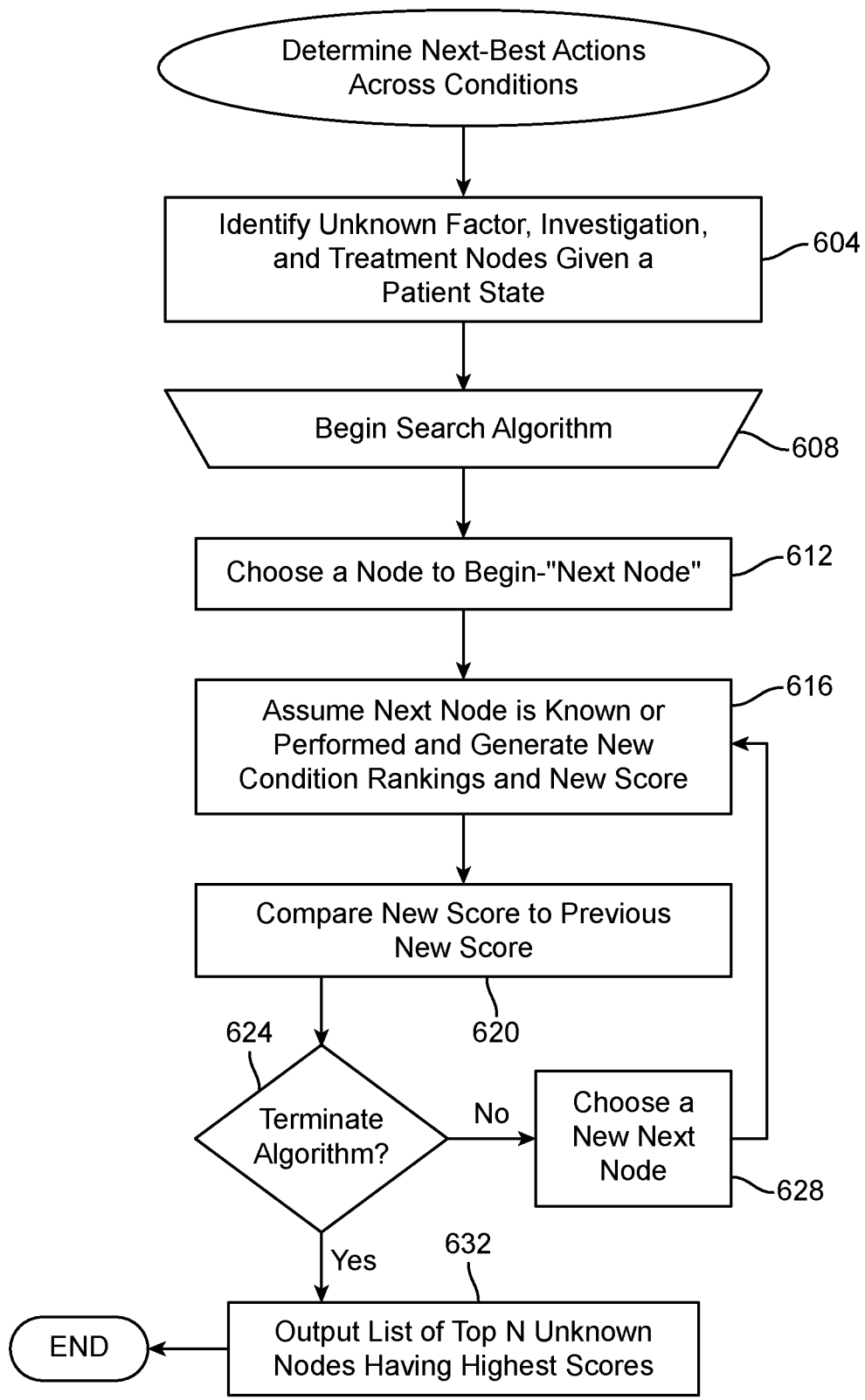
FIG. 7 is a flow diagram describing how the next-best actions across conditions are determined based upon the patient's state.

Further, once the patient has answered the question, or received laboratory or examination results back, this new information may be entered back into the system in order to execute the flows of FIG. 5, 6 or 7 in order to generate new results.

Display Ranked Conditions and Next-Best Actions

Figure 8A:
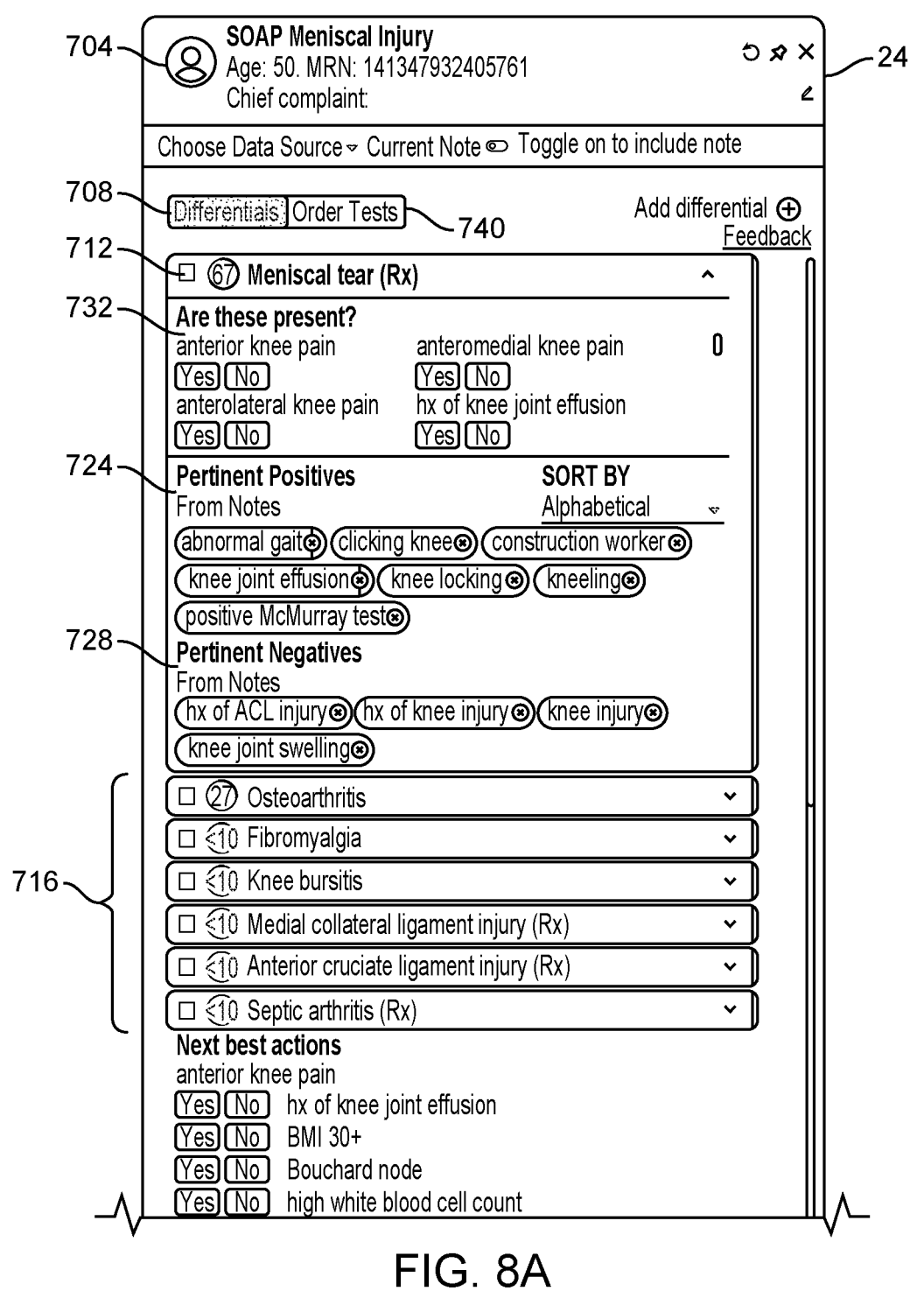

FIG. 8A illustrates a display of ranked conditions and also next-best actions per condition. Shown is a user interface of diagnostic glass application 24 having patient information 704, a selection 708 of whether to display differential diagnoses each with their next-best actions (factors) or the differential diagnoses each with their next-best actions (investigations). The clinician has selected differentials with factors 708. Shown are the differential diagnoses 712 and 716 for this patient listed in order of their likely probability; in this embodiment each condition is preceded by its probability (meniscal tear-67%, osteoarthritis-27%, etc.), although the probability or ranking need not be explicitly present. Although other information is present, the above shows the output of step 432 from FIG. 5.

Also shown is other information relevant to the output of step 528 from FIG. 6. Shown are factors from the patient's record 720 including pertinent positives and pertinent negatives (not shown, but the clinician can scroll down to see them). Here, the clinician has selected factors to be shown but may also select vital signs, laboratory results or other examinations. Shown at 724 and 728 are the pertinent positive and negative factors and investigations that pertain to condition 712; in other words, those known factors and investigations that most likely indicate the associated condition 712. These may be ordered alphabetically or by rank. Although not shown, if any of the other conditions 716 are expanded, their pertinent positives and negatives would also be shown.

The next-best actions 732 for condition 712 are shown below that condition and are those factors which are not yet known or have not yet been performed. These may be listed as a group of the top actions to ask about or perform next or may be listed in order of their likelihood of indicating the associated condition, with or without an explicit ranking. The clinician may review and perform one of these actions 732; once he or she inputs whether the factor is now present or not, then the platform may execute the steps of FIG. 6 in order to display new conclusions based upon the new information in step 528.

At any time, a clinician reviewing this display may access the citations relied upon for the conclusions present. By way of example, by clicking upon a particular condition such as condition 712, a window is opened presenting a view of the graph database including that condition, such as a view shown in FIG. 4A (another view is shown in FIG. 4B). From here, the clinician can see the various factor groups with their names and may select one of these factor groups to understand why the factors of this group are indicative of the medical condition. Once selected, the factor group is displayed such as shown at 372, and the clinician may review the rank of the group, criteria, names of subsumed EDFs or diagnostic factors, and see the link to the citation, such as the link to citation 378. The clinician may then click upon this link to reveal the actual citation such as shown at 832 in FIG. 9B. The clinician may then review the actual reference of the citation using the enclosed URL (or other unique identifier) in order to assure himself or herself that the conclusion of the condition 712 is accurate. Accordingly, citations are built into the graph database, are transparent, and may be accessed easily by a clinician when reviewing results in order to provide confidence in the conclusion. A citation may be accessed for an investigations group (such as citation 388) in a similar manner. Similarly, citations may also be accessed from any of the outputs of FIG. 8B or FIG. 8C.

Figure 8B:
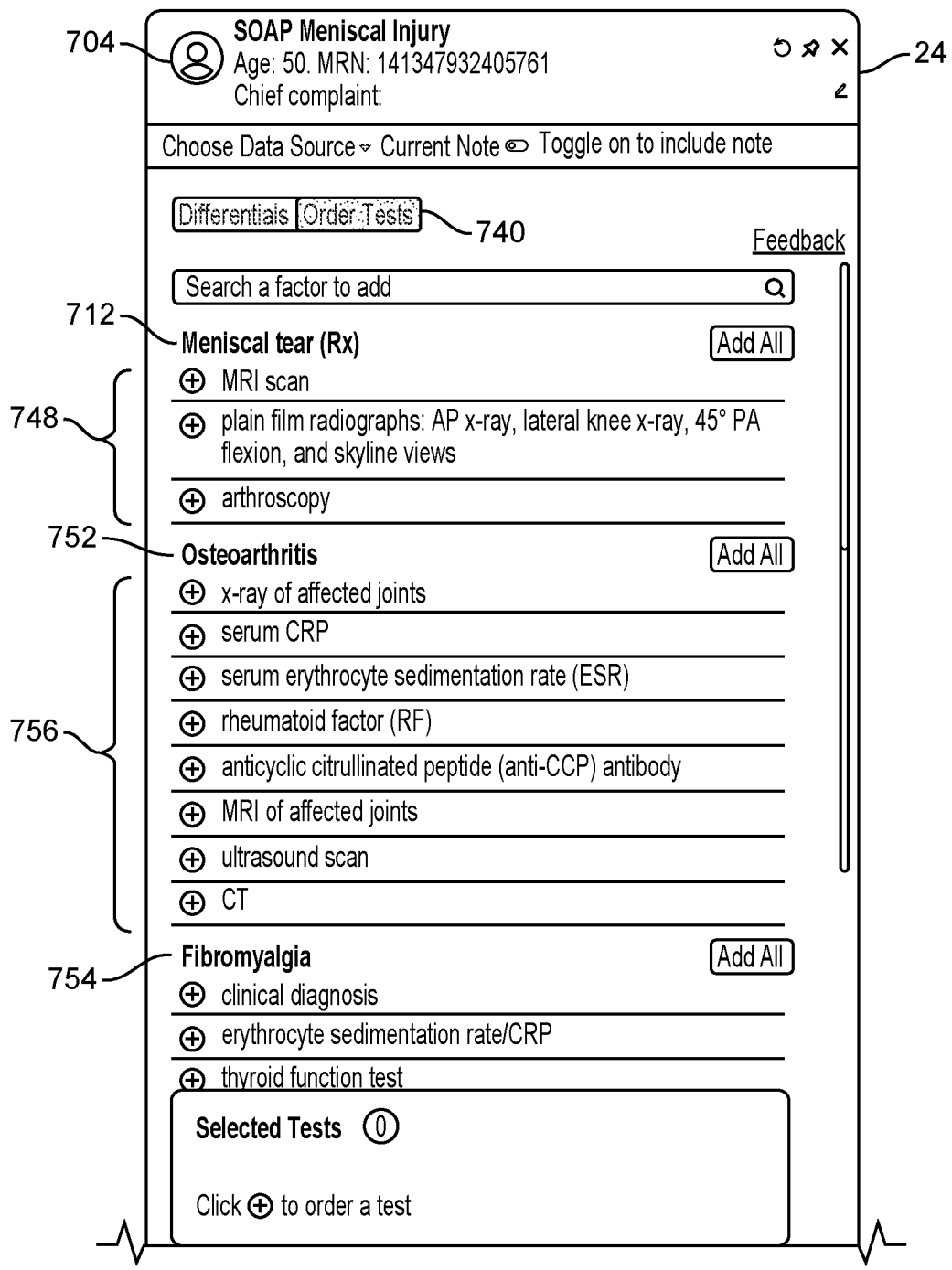
FIG. 8B illustrates a display of ranked conditions and also next-best actions per condition.

FIG. 8B illustrates a display of ranked conditions and also next-best actions per condition. Shown is the diagnostic glass 24 but this time the clinician has selected tests 740 in order to display the laboratory tests or examinations which are the next-best actions. Shown are conditions 712, 752 and 754 from before, except that in this view each condition is followed by the recommended laboratory tests or examinations which have not yet been performed and which are ordered by the likelihood that they will indicate or rule out the associated condition. By way of example, examinations 748 are recommended for condition 712, examinations and laboratory tests 756 are recommended for condition 752, and condition 754 is followed by its recommended tests and examinations. These investigations may be ordered by which most likely indicates or could rule out the associated condition, may or may not have an explicit ranking alongside each one, may be listed as a group with no explicit or implicit rankings, may be listed by overall cost which as explained below may include a combination of dollar cost, time to administer and risk to the patient.

Although not shown, the clinician may select both options 708 and 740 in which case the next-best actions of 732 and 748 for condition 712 will be listed together, and may be listed by rank of likelihood of indicating the particular condition (factors and investigations are mixed), grouped by factors or investigations, etc.

Figure 8C:
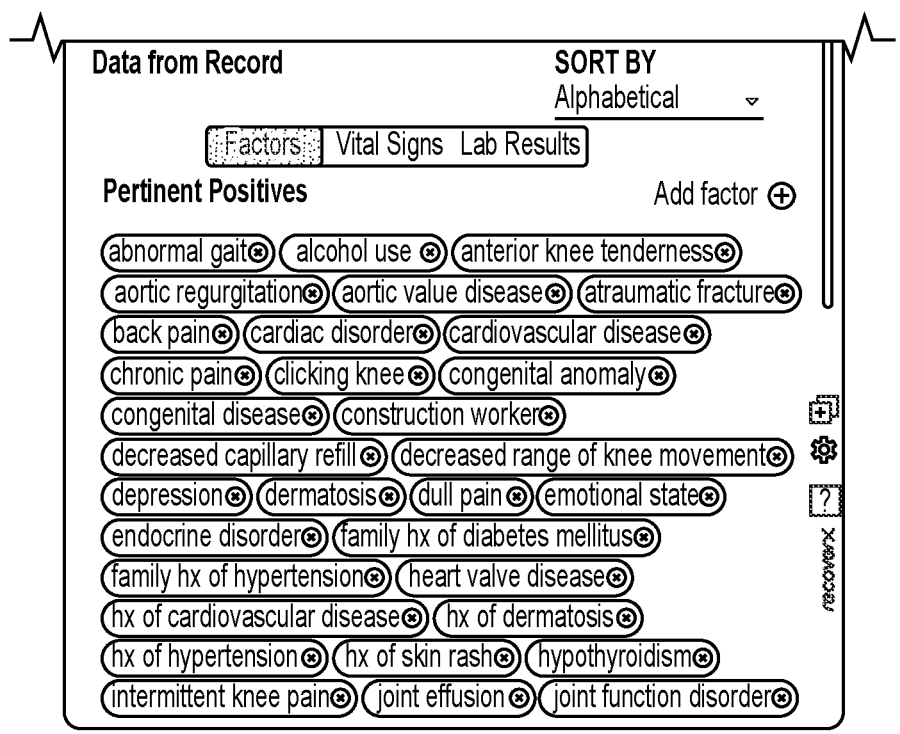
FIG. 8C illustrates a display of next-best actions across conditions.

FIG. 8C illustrates a display of next-best actions across conditions. Shown is the diagnostic glass 24 similar to that of FIG. 8A. Shown is the patient's information 704, a selection of differential diagnoses 708, and the next-best actions specific to condition 712. In addition, in order to display the output of step 632 of FIG. 7, shown are next-best actions 760 which are those next-best factors to ask about or next-best laboratory tests or examinations to be performed across all conditions 712 and 716. In other words, these are factors which are not yet known to be present or not present, and laboratory tests or examinations which have not yet been performed, and which if known or performed, would be the best at concluding which is the patient's most likely current condition. For example, if one or more these actions are performed and the results are input at 760, the platform will re-execute any of the flow diagrams of FIG. 5, 6 or 7, and may conclude that osteoarthritis is more probable than a meniscal tear (depending upon the results of the actions 760). Or, condition 712 may be even more certain and will have a higher probability than 67%.

Example Transformation

Figure 10:
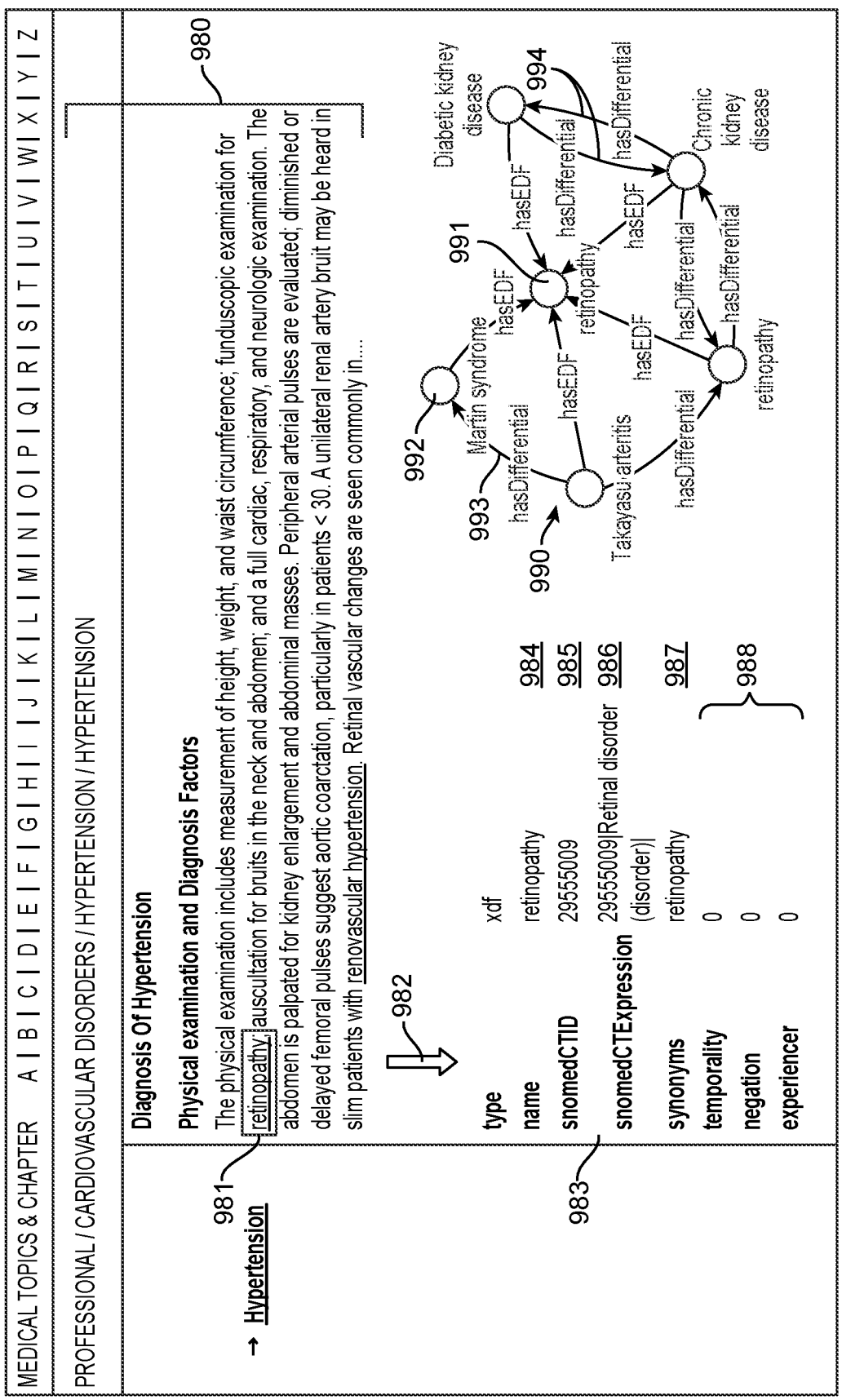
FIG. 10 is an example transformation of evidence-based text to computational data.

FIG. 10 is an example transformation of evidence-based text to computational data. Shown is a portion of a medical evidence source 980 for the condition hypertension. The portion lists the condition, various diagnostic factors such as retinopathy 981, and a brief description. Although not shown, the frequency of each diagnostic factor for this condition may also be listed indicating its rank. Once this portion for retinopathy is transformed 982 (or translated) as discussed above with reference to FIG. 3 then the diagnostic factor retinopathy for hypertension may be represented as an elemental diagnostic factor (EDF) 983. This node includes its name 984, an ontology identifier 985, an ontology expression 986, any number of synonyms 987, and specific temporality, negation and experiencer attributes 988 having a binary value. This EDF 983 for retinopathy may then be represented and used for computational purposes in a graph database 990 having the retinopathy data 983 represented as a node 991. As shown, node 991 serves as an EDF for any number of conditions such as Marfan syndrome 992. These conditions may also have differential diagnoses links 993 and 994 between them as well. Accordingly, by virtue of retinopathy node 991 being elemental and independent, and not including condition-specific attributes, it may be used as a diagnostic factor node for any of a number of conditions as shown for computational purposes.

Computer System Embodiment

Figure 11A:
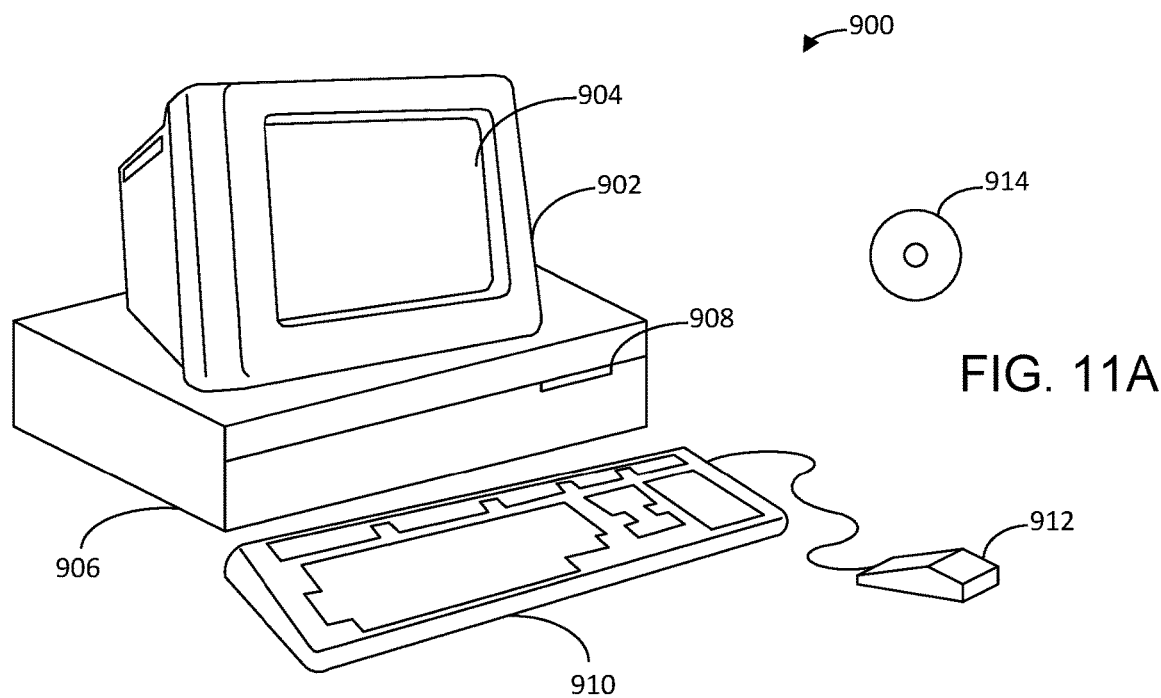
FIGS. 11A and 11B illustrate a computer system suitable for implementing embodiments of the present invention.
Figure 11B:
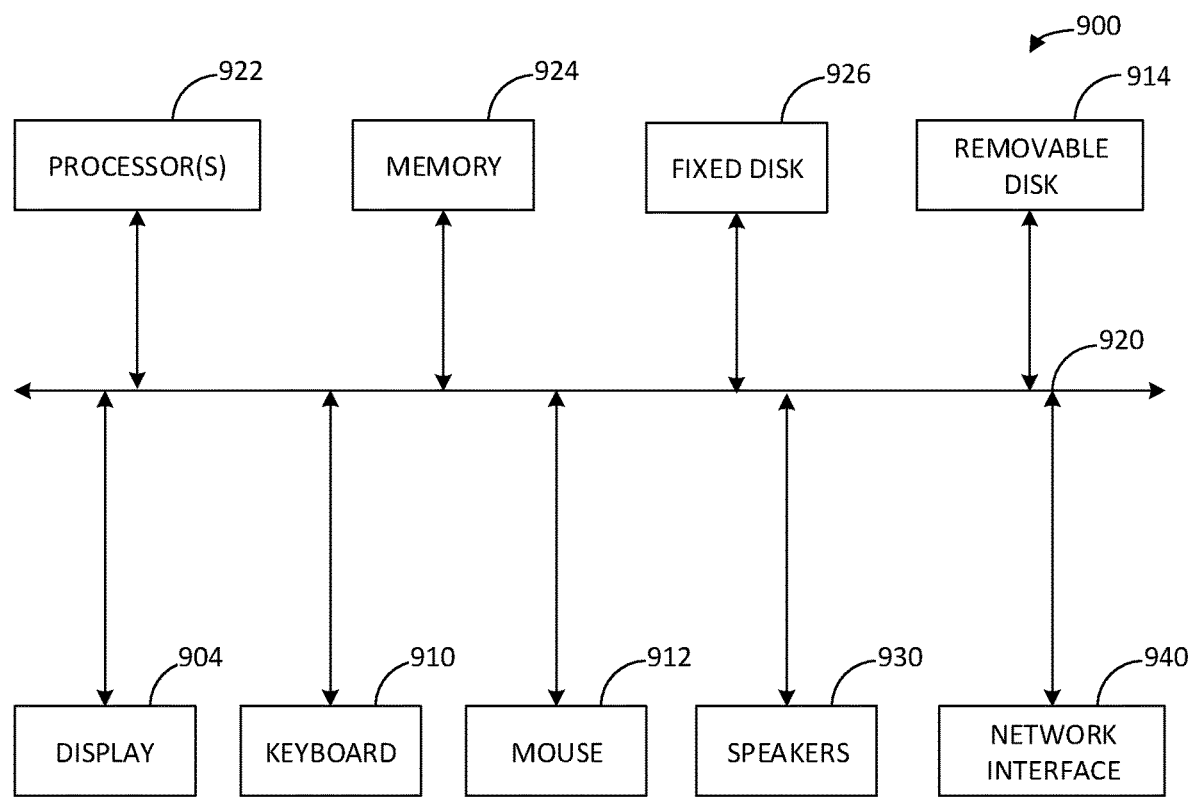

FIGS. 11A and 11B illustrate a computer system 900 suitable for implementing embodiments of the present invention. FIG. 11A shows one possible physical form of the computer system. Of course, the computer system may have many physical forms including an integrated circuit, a printed circuit board, a small handheld device (such as a mobile telephone or PDA), a personal computer or a super computer. Computer system 900 includes a monitor 902, a display 904, a housing 906, a disk drive 908, a keyboard 910 and a mouse 912. Disk 914 is a computer-readable medium used to transfer data to and from computer system 900.

FIG. 11B is an example of a block diagram for computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner Both of these types of memories may include any suitable of the computer-readable media described below. A fixed disk 926 is also coupled bi-directionally to CPU 922; it provides additional data storage capacity and may also include any of the computer-readable media described below. Fixed disk 926 may be used to store programs, data and the like and is typically a secondary mass storage medium (such as a hard disk, a solid-state drive, a hybrid drive, flash memory, etc.) that can be slower than primary storage but persists data. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps. Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher-level code that are executed by a computer using an interpreter.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

We claim:

1. A method of determining a differential diagnosis for a patient, said method comprising:
   receiving, at a diagnostic software application, health information of a patient from a computer system during a patient encounter or when said patient is not present, wherein said diagnostic software application includes a user interface;
   automatically extracting patient diagnostic factors known to be present or absent in said patient from said received health information;
   automatically matching said patient diagnostic factors to diagnostic factor nodes in a knowledge base, said diagnostic factor nodes being linked to medical condition nodes in said knowledge base;
   automatically ranking medical conditions that are each associated with one of said medical condition nodes based upon said diagnostic factor nodes;
   displaying on a computing device said ranked medical conditions;
   assuming that a diagnostic factor of said patient not known to be present or absent is now known to be present or absent, that a laboratory test of said patient not performed has now been performed or that an examination of said patient not performed has now been performed;
   automatically generating a new ranking of said medical conditions based upon said assuming, and determining at least one next-best action on the basis of said new ranking of said medical conditions; and
   displaying said next-best action on said computing device.

2. A method as recited in claim 1 wherein said next-best action is said diagnostic factor of said patient not yet known to be present or absent, said laboratory test of said patient not yet performed or said examination of said patient not yet performed.

3. A method as recited in claim 1 further comprising:
   displaying on said computing device said ranked medical conditions in order of rank.

4. A method as recited in claim 1 wherein said displaying said ranked medical conditions occurs before a patient encounter with a clinician.

5. A method as recited in claim 1 wherein said extracting further comprises:
   extracting patient diagnostic factors known to be present or absent in said patient from an electronic health record of said patient.

6. A method as recited in claim 1 wherein said diagnostic software application executes upon a cloud-based computer, and wherein said displaying said ranked medical conditions occurs within a Web browser of said computing device.

7. A method as recited in claim 1 wherein each of said rankings indicates a probability that one of said medical conditions is due to said patient diagnostic factors.

8. A method as recited in claim 1 wherein said health information is received from said computer system of said patient via an online chat, via an online session, or via a video call.

9. A method as recited in claim 1 wherein said health information is received from an electronic health record (EHR) of said computer system or from said computer system via a query API (application programming interface) of said knowledge base.

10. A method of determining a differential diagnosis for a patient, said method comprising:
    receiving, at a diagnostic software application, health information of a patient from a computer system during a patient encounter or when said patient is not present, wherein said diagnostic software application includes a user interface;
    automatically extracting patient diagnostic factors known to be present or absent in said patient from said received health information;
    automatically matching said patient diagnostic factors to diagnostic factor nodes in a knowledge base, said diagnostic factor nodes being linked to medical condition nodes in said knowledge base;
    automatically ranking medical conditions that are each associated with one of said medical condition nodes based upon said diagnostic factor nodes;
    displaying on a computing device said ranked medical conditions;
    automatically ranking said medical conditions again by assuming that an unknown diagnostic factor of said patient currently not known to be present or absent is now known to be present or absent, that a laboratory test of said patient not performed has now been performed or that an examination of said patient not performed has now been performed in order to obtain newly-ranked medical conditions;
    automatically determining that a next-best action is said unknown diagnostic factor, said laboratory test or said examination of said patient based upon said newly-ranked medical conditions; and
    displaying said next-best action on said computing device.

11. A method as recited in claim 10 wherein said health information is received from said computer system of said patient via an online chat, via an online session, or via a video call.

12. A method as recited in claim 10 wherein said health information is received from an electronic health record (EHR) of said computer system or from said computer system via a query API (application programming interface) of said knowledge base.

13. A method as recited in claim 10 wherein said diagnostic software application executes upon a cloud-based computer, and wherein said displaying said ranked medical conditions occurs within a Web browser of said computing device.

14. A method of outputting a next-best action for a patient, said method comprising:
    receiving, at a knowledge graph, patient diagnostic factors known to be present or absent in said patient;
    automatically matching said patient diagnostic factors to diagnostic factor nodes in said knowledge graph, said diagnostic factor nodes being linked to medical condition nodes in said knowledge graph, each medical condition node indicating a medical condition;
    automatically ranking said medical conditions by assuming that an unknown diagnostic factor of said patient currently not known to be present or absent is now known to be present or absent, in order to obtain ranked medical conditions;
    automatically determining that a next-best action is said unknown diagnostic factor of said patient based upon said ranked medical conditions; and
    outputting said next-best action to a diagnostic software application of a computing device during a patient encounter or when said patient is not present, wherein said diagnostic software application includes a user interface.

15. A method as recited in claim 14 further comprising:
generating a score for said unknown diagnostic factor that represents a change in a differential diagnosis between said ranked medical conditions when said unknown diagnostic factor is now known to be present or absent; and
determining that said next-best action is said unknown diagnostic factor based upon said score.

16. A method as recited in claim 14 further comprising:
ranking said medical conditions by assuming that said unknown diagnostic factor of said patient currently not known to be present or absent is now known to be present or absent, that a laboratory test of said patient not performed has now been performed or that an examination of said patient not performed has now been performed in order to obtain said ranked medical conditions; and
determining that said next-best action is said unknown diagnostic factor of said patient, said laboratory test or said examination of said patient based upon said ranked medical conditions.

17. A method as recited in claim 14 further comprising:
outputting said next-best action from said knowledge graph to said computing device via an application programming interface (API).

18. A method as recited in claim 14 further comprising:
performing a search algorithm that assumes that a plurality of unknown diagnostic factors of said patient each currently not known to be present or absent are each now known to be present or absent, in order to obtain a score for said each unknown diagnostic factor;
determining a plurality of next-best actions based upon said scores, each of said next-best actions being one of said unknown diagnostic factors of said patient assumed to be known present or absent; and
outputting said next-best actions to a computing device.

19. A method as recited in claim 14 wherein said patient diagnostic factors are received from a computer of a patient via an online chat, via an online session, or via a video call.

20. A method as recited in claim 14 wherein said patient diagnostic factors are received from an electronic health record (EHR) of a computer system or from a computer system via a query API (application programming interface) of said knowledge graph.

\* \* \* \* \*